(12) United States Patent
Shankar et al.

(10) Patent No.: US 11,488,714 B2
(45) Date of Patent: Nov. 1, 2022

(54) MACHINE LEARNING FOR COLLABORATIVE MEDICAL DATA METRICS

(71) Applicant: HealthPals, Inc., San Mateo, CA (US)

(72) Inventors: Sushant Shankar, Oakland, CA (US); Rajesh Dash, San Francisco, CA (US)

(73) Assignee: HealthPals, Inc., Redwood City, CA (US)

( * ) Notice: Subject to any disclaimer, the term of this patent is extended or adjusted under 35 U.S.C. 154(b) by 45 days.

(21) Appl. No.: 16/057,024

(22) Filed: Aug. 7, 2018

(65) Prior Publication Data

US 2018/0342323 A1 Nov. 29, 2018

Related U.S. Application Data

(63) Continuation-in-part of application No. 15/467,378, filed on Mar. 23, 2017.
(Continued)

(51) Int. Cl.
*G16H 50/20* (2018.01)
*G16H 50/70* (2018.01)
(Continued)

(52) U.S. Cl.
CPC ............ *G16H 50/20* (2018.01); *G06N 5/025* (2013.01); *G06N 7/005* (2013.01); *G06N 20/00* (2019.01);
(Continued)

(58) Field of Classification Search
CPC ......... G16H 50/20; G16H 10/60; G16H 50/70
See application file for complete search history.

(56) References Cited

U.S. PATENT DOCUMENTS 8,015,136 B1 9/2011 Baker et al.
8,956,287 B2 2/2015 Zdeblick et al.
(Continued)

FOREIGN PATENT DOCUMENTS

WO WO2014186838 A1 11/2014

OTHER PUBLICATIONS

Thornley, S., et al. "Using directed acyclic graphs for investigating causal paths for cardiovascular disease." J Biometrics Biostatistics 4 (2013): 182.
(Continued)

*Primary Examiner* — Sheetal R Paulson
(74) *Attorney, Agent, or Firm* — Adams Intellex, PLC

(57) ABSTRACT

A medical knowledge database including medical knowledge information, medical diagnoses, and medical treatments, is used for machine learning for collaborative medical data metrics. Medical data is collected from a plurality of clinicians serving a first plurality of patients and assembling a medical knowledge database that includes medical knowledge information, medical diagnoses, and medical treatments. The medical knowledge database is a function of demographics and comprises a medical probabilistic rules graph. The medical knowledge database is augmented based on further medical data collected from a second plurality of clinicians. The further medical data is based on individual patient treatment outcomes collected by the second plurality of clinicians. Medical data from a further patient is applied to the medical probabilistic rules graph. A medical diagnosis is provided, based on the medical data applied from a further patient to the rules graph. The medical diagnosis is used to institute a treatment plan.

27 Claims, 14 Drawing Sheets

Related U.S. Application Data

(60) Provisional application No. 62/541,968, filed on Aug. 7, 2017, provisional application No. 62/312,226, filed on Mar. 23, 2016.

(51) Int. Cl.

| | | |
|---|---|---|
| *G16H 10/60* | (2018.01) | |
| *G16H 20/60* | (2018.01) | |
| *G06N 20/00* | (2019.01) | |
| *G16H 20/30* | (2018.01) | |
| *G06N 5/02* | (2006.01) | |
| *G06N 7/00* | (2006.01) | |
| *G16H 50/30* | (2018.01) | |
| *G16H 20/10* | (2018.01) | |
| *G06K 9/62* | (2022.01) | |
| *G16H 80/00* | (2018.01) | |
| *G16H 15/00* | (2018.01) | |
| *G16H 10/40* | (2018.01) | |
| *G06N 3/02* | (2006.01) | |
| *G06F 16/35* | (2019.01) | |
| *G06N 3/08* | (2006.01) | |
| *G06N 3/04* | (2006.01) | |

(52) U.S. Cl.
CPC ............. *G16H 10/60* (2018.01); *G16H 20/30* (2018.01); *G16H 20/60* (2018.01); *G16H 50/30* (2018.01); *G16H 50/70* (2018.01); *G06F 16/35* (2019.01); *G06K 9/6262* (2013.01); *G06K 9/6278* (2013.01); *G06N 3/02* (2013.01); *G06N 3/0454* (2013.01); *G06N 3/082* (2013.01); *G06N 3/088* (2013.01); *G16H 10/40* (2018.01); *G16H 15/00* (2018.01); *G16H 20/10* (2018.01); *G16H 80/00* (2018.01)

(56) References Cited

U.S. PATENT DOCUMENTS

| | | |
|---|---|---|
| 8,977,347 B2 | 3/2015 | Mestha et al. |
| 9,042,970 B2 | 5/2015 | Lu et al. |
| 9,119,554 B2 | 9/2015 | Zdeblick et al. |
| 2008/0201280 A1 | 8/2008 | Martin et al. |
| 2014/0350967 A1 | 11/2014 | Geleijnse et al. |
| 2015/0051461 A1 | 2/2015 | Dalal et al. |
| 2015/0087926 A1 | 3/2015 | Raz et al. |
| 2016/0055307 A1 | 2/2016 | Macoviak et al. |
| 2016/0371446 A1 | 12/2016 | Otin |
| 2017/0024640 A1 | 1/2017 | Deng et al. |
| 2017/0076052 A1 | 3/2017 | Phillips et al. |

OTHER PUBLICATIONS

Jordan, Michael I., and Yair Weiss. "Probabilistic inference in graphical models." Handbook of neural networks and brain theory (2002).

Koller, Daphne, et al. "Graphical models in a nutshell." Introduction to statistical relational learning (2007): 13-55.

HEALTH CARE

CLINIC VIEW
- Patients

*All Patients*
Population Health

Treatments  Biometrics  Quality Measures

PATIENT

Configure Columns

| NAME | ETHNICITY | QRISK2 (ABS) | BMI | BLOOD PRESSURE | TC/HDL RATIO | LDL | LDL PARTICLE NUMBER | LP(A) | APO B |
|---|---|---|---|---|---|---|---|---|---|
| LAKSHAY KHAN | INDIAN | 14.0% | 29.67 | 140/89 | 4.7 | 186 | 1987 | 14 | 135 |
| JAMIE SMITH | WHITE | 8.1% | 27.34 | 130/80 | 6.78 | 195 | 1404 | 36 | 74 |
| ZARA KUMAR | INDIAN | 9.4% | 32.03 | 142/95 | 11.3 | 136 | 2139 | 60 | 92 |
| JANIE BALLARD | WHITE | 1.0% | 23.45 | 122/76 | 3.4 | 69 | 887 | 15 | 75 |
| AHANA CHATTERJEE | INDIAN | 23.0% | 26.92 | 136/84 | 9.8 | 227 | 2483 | 22 | 175 |
| HARIKIRAN SHANKER | INDIAN | 6.5% | 24.68 | 128/84 | 5.2 | 122 | 1023 | 16 | 110 |
| JAYESH PATEL | INDIAN | 1.4% | 23.04 | 119/78 | 3.5 | 70 | 946 | 54 | 85 |
| LAKSHAY SENGUPTA | PAKISTANI | 4.0% | 25.07 | 133/96 | 4.3 | 92 | 1189 | 119 | 65 |
| SHAWN NASH | WHITE | 8.0% | 29.04 | 145/91 | 9.2 | 134 | 1296 | 98 | 112 |
| REYANSH NARULA | INDIAN | 13.6% | 29.67 | 140/89 | 4.7 | 186 | 1987 | 14 | 135 |
| ANAV ZACHARIAH | INDIAN | 9.4% | 32.03 | 142/95 | 11.3 | 136 | 2139 | 60 | 92 |
| VIVAAN MAJUMDAR | INDIAN | 18.5% | 26.92 | 136/84 | 9.8 | 227 | 2483 | 138 | 175 |
| YASHVI BHATIA | INDIAN | 6.5% | 24.68 | 128/84 | 5.2 | 122 | 1023 | 16 | 110 |

FIG. 8

MACHINE LEARNING FOR COLLABORATIVE MEDICAL DATA METRICS

RELATED APPLICATIONS

This application claims the benefit of U.S. provisional patent application "Machine Learning for Collaborative Medical Data Metrics" Ser. No. 62/541,968, filed Aug. 7, 2017.

This application is also a continuation-in-part of U.S. patent application "Self-Learning Clinical Intelligence System Based on Biological Information and Medical Data Metrics" Ser. No. 15/467,378, filed Mar. 23, 2017, which claims the benefit of U.S. provisional patent application "Self-Learning Clinical Intelligence System Based on Biological Information and Medical Data Metrics" Ser. No. 62/312,226, filed Mar. 23, 2016.

Each of the foregoing applications is hereby incorporated by reference in its entirety.

FIELD OF ART

This application relates generally to machine-learned collaborative medical diagnosis and more particularly to machine learning for collaborative medical data metrics.

BACKGROUND

Health care is a topic that elicits strong and passionate opinions and reactions from people around the world. While in some countries health care services are provided, to varying degrees, to residents through government agencies, in other countries, those seeking health care services are left to fend for and pay for themselves. Doctors and clinics may be located far from those people needing medical assistance and services, forcing those people to arrange transportation which may even include walking to the clinics. Once people arrive at the clinics, they may need to wait long periods of time before they are able to see a medical professional. The medical professional that sees a given patient may or may not be able to diagnose a particular disease or condition. Once the medical professional is seen, there remain the questions of where to obtain recommended treatments, and where to obtain medications that support the treatments. Of the many aspects of health care which people choose to complain, most people can agree that efficiency in health care is paramount. Health care efficiency can include correctly and quickly diagnosing a disease or condition and recommending an effective treatment. Effective treatment can include drug therapies, lifestyle change recommendations, and counseling, among others. New treatments, therapies, drugs, and recommendations are released at a rapid pace. New medical conditions are identified or their identifications refined, new treatments are developed to treat certain diseases or conditions, new drugs are developed, and new counseling recommendations are made, among other improvements. The pace of change in the many medical fields is rapid and relentless.

Doctors and other health care providers treat hundreds of millions of patients for myriad health situations. The patient health scenarios can range from illness and disease to injury and trauma. Patients are treated based on the personal knowledge and experience of the doctors and health care providers, plus consideration of medical data collected from wide ranging sources. Medical data is ubiquitous today and is used for formal and informal purposes. Formal uses of medical data include electronic medical records (EMR), which are collected every time a patient visits her or his doctor, analysis of clinical data from various research and clinical studies, and so on. Informal examples of medical data can include that data kept by an individual to track weight, blood pressure, blood sugar, number of cigarettes smoked, number of alcoholic beverages consumed per week, amount of exercise each day, and so on. Whatever the source of the data, the data is stored for current and future use. The stored medical data is used for research and analysis purposes, as well as to provide health care to an individual, to track occurrences of medical conditions and various diseases such as infectious diseases, and to track the transmissions of infections, diseases, etc.

The clinicians and health care providers treat their patients based on the clinician's or health care provider's knowledge of medical best practices, as well as the constraints of the particular medical situation. The constraints include such factors as availability of specialists, access to appropriate diagnostic equipment, or even availability of drugs. These kinds of scenarios are occurring many, many times each day around the world. Each scenario has a medical condition, a treatment, and an eventual outcome of the treatment. Each element of every scenario has the potential to add to patient medical records and to form a more comprehensive view of the patient's overall health and wellness.

SUMMARY

Results collected from medical experiments, drug trials, and laboratory research, among other sources, are released every day. The overall amount of data that is published or shared is very large, as is the number of journals, websites, databases, and so on, to which the data is published. The amount of data, particularly new data, can be daunting to a clinician. In order for the new data to be useful, the data must be analyzed, procedures or treatments updated or new procedures or new treatments developed, drug therapies updated or learned, lifestyle change recommendations amended, counseling approaches updated, etc. Given that clinicians and other medical professionals are extremely busy, the clinicians and others are typically time-limited in their abilities to study and learn from the new data. Access to certain datasets may be limited to certain subscribers, hospital systems, and the like. Further, the data formats for the contents of disparate databases may be incompatible. Machine learning techniques can be applied to the data to identify trends, new or emerging therapies, drug therapy recommendations, and so on.

Medical data is collected from a plurality of clinicians serving a first plurality of patients. A medical knowledge database is assembled that includes medical knowledge information, medical diagnoses, and medical treatments. The medical knowledge database is a function of demographics such as age, gender, race, and family history, and includes a medical probabilistic rules graph. The medical knowledge database is augmented based on further medical data collected from a second plurality of clinicians. The further medical data is based on individual patient treatment outcomes collected by the second plurality of clinicians. Medical data from a further patient is applied to the medical probabilistic rules graph that was augmented to produce a medical diagnosis. An impact is projected for the further patient that factors in a change in medical treatment, where the impact that is projected includes a change in risk level for the further patient. The projecting of an impact on the further patient can be due to a change in patient behavior. A treatment plan is generated for the further patient based on the medical probabilistic rules graph that was augmented.

In disclosed techniques, a computer-implemented method for machine-learned collaborative medical diagnosis comprises: collecting medical data from a plurality of clinicians serving a first plurality of patients and assembling a medical knowledge database that includes medical knowledge information, medical diagnoses, and medical treatments, wherein the medical knowledge database is a function of demographics and comprises a medical probabilistic rules graph; augmenting the medical knowledge database based on further medical data collected from a second plurality of clinicians, wherein the further medical data is based on individual patient treatment outcomes collected by the second plurality of clinicians; applying medical data from a further patient to the medical probabilistic rules graph that was augmented; and providing a medical diagnosis, based on the medical data applied from a further patient to the medical probabilistic rules graph.

In embodiments, the medical diagnosis is used to institute a treatment plan. In embodiments, the treatment plan that was instituted comprises a change in treatment. In other embodiments, the medical diagnosis comprises a list of evidence-based treatments, lab work recommendations, diagnostic recommendations, or lifestyle interventions. And in yet other embodiments, the medical diagnosis provides evidence-based gaps in care or errors in treatment plans.

Various features, aspects, and advantages of various embodiments will become more apparent from the following further description.

BRIEF DESCRIPTION OF THE DRAWINGS

The following detailed description of certain embodiments may be understood by reference to the following figures wherein:

FIG. 8 illustrates an example of ethnicity and risk factors.

DETAILED DESCRIPTION

Figure 1:
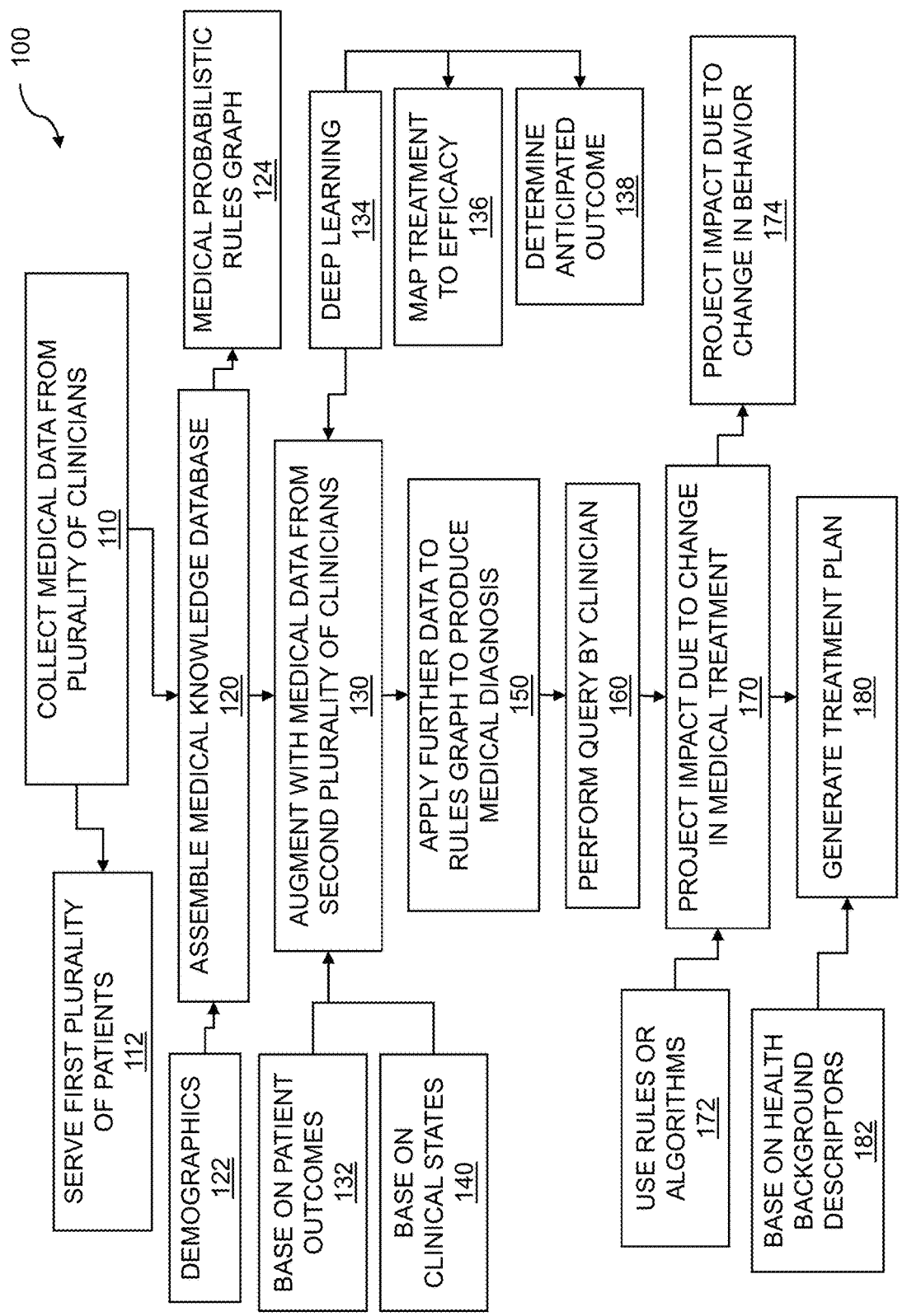
FIG. 1 is a flow diagram for machine learning for collaborative medical data metrics.

Medical research, clinical trials, and other medical investigations regularly yield new recommendations to doctors and other health care providers relating to diagnosis and treatment of a wide diversity of medical conditions. The medical conditions can be many and varied, and can include diseases such as cardiovascular disease (CVD), cancer, diabetes, kidney disease, liver disease, and so on. CVD, for example, can result from various risk factors such as family history of CVD, a patient's own biological factors such as body weight, blood pressure, blood sugar, and unhealthy behaviors such as smoking and alcohol consumption. The recommendations can be based on medical data collected from clinicians, where the medical data includes medical knowledge information, medical diagnoses, and medical treatments. By collecting additional information from further groups of clinicians, the medical knowledge base can be augmented. The augmenting of the database can be based on individual patient treatment outcomes, whether positive or negative. The augmented medical data can be applied to further patients to produce medical diagnoses. Based on the medical diagnoses and the data in the medical knowledge base, treatment recommendations for the patients can be made. The treatment recommendations can include projections of impacts of various treatments on the patients, including changing treatment, changing patient behaviors, and so on. The projections of impacts can also include impacts on various risk factors.

Techniques for machine-learned collaborative medical diagnosis are disclosed. Medical data is collected from a plurality of clinicians serving a first plurality of patients and a medical knowledge database is assembled that includes medical knowledge information, medical diagnoses, and medical treatments, wherein the medical knowledge database is a function of demographics and comprises a medical probabilistic rules graph. The medical knowledge database is augmented based on further medical data collected from a second plurality of clinicians, wherein the further medical data is based on individual patient treatment outcomes collected by the second plurality of clinicians. Medical data from a further patient is applied to the medical probabilistic rules graph that was augmented to produce a medical diagnosis.

In embodiments, a computer program product embodied in a non-transitory computer readable medium for machine learned collaborative medical diagnosis, the computer program product comprising code which causes one or more processors to perform operations of: collecting medical data from a plurality of clinicians serving a first plurality of patients and assembling a medical knowledge database that includes medical knowledge information, medical diagnoses, and medical treatments, wherein the medical knowledge database is a function of demographics and comprises a medical probabilistic rules graph; augmenting the medical knowledge database based on further medical data collected from a second plurality of clinicians, wherein the further medical data is based on individual patient treatment outcomes collected by the second plurality of clinicians; applying medical data from a further patient to the medical probabilistic rules graph that was augmented; and providing a medical diagnosis, based on the medical data applied from a further patient, to the medical probabilistic rules graph.

In other embodiments, a computer system for machine learned collaborative medical diagnosis comprising: a memory which stores instructions; one or more processors attached to the memory wherein the one or more processors, when executing the instructions which are stored, are configured to: collect medical data from a plurality of clinicians serving a first plurality of patients and assembling a medical knowledge database that includes medical knowledge information, medical diagnoses, and medical treatments, wherein the medical knowledge database is a function of demographics and comprises a medical probabilistic rules graph; augment the medical knowledge database based on further medical data collected from a second plurality of clinicians, wherein the further medical data is based on individual patient treatment outcomes collected by the second plurality of clinicians; and apply medical data from a further patient to the medical probabilistic rules graph that was augmented; and provide a medical diagnosis, based on the medical data applied from a further patient to the medical probabilistic rules graph.

FIG. 1 is a flow diagram for machine learning for collaborative medical data metrics. The flow 100, or portions thereof, can be implemented using a mobile device, a server, a cloud processor, a mesh processor, and so on. The flow 100, or portions thereof, can be implemented using one or more processors. The flow 100 describes a machine learning system for collaborative medical data metrics. The flow 100 includes collecting medical data from a plurality of clinicians 110 serving a first plurality of patients 112. The plurality of clinicians can be colocated at one location, affiliated across a hospital network, working in related fields, etc. The patients 112 can be patients visiting with their primary care physicians (PCP), visiting specialists, in emergency rooms, in critical care units, and so on. The medical data can include data from office visits, a clinical practice, clinical trials, research trials, etc. The medical data can include patient demographic data, morphometric data, vital statistics, family histories, treatment histories, and the like. The flow 100 includes assembling a medical knowledge database 120 that includes medical knowledge information, medical diagnoses, and medical treatments. The medical knowledge database can be stored on a local server, a remote server, over a distributed storage service such as mesh storage, on a cloud server, and so on. The medical knowledge information can include medical best practices. The medical knowledge information relating to best practices can include best practices for diagnosing clinical states, best practices for treating clinical states, and so on. In embodiments, the medical knowledge database can be a function of demographics 122 and can include a medical probabilistic rules graph 124. The demographics 122 can include age, gender, race, ethnicity, educational level, household income, partnership status, occupation, etc. The medical probabilistic rules graph can include variables and factors. The variables can include evidence variables with known values, and query variables with unknown values. The factors can define relationships between and among variables. The relations can include probabilities. The medical knowledge database can include medical best practices. The medical best practices can be related to diagnosing clinical states, treating clinical states, etc.

The flow 100 includes augmenting the medical knowledge database based on further medical data collected from a second plurality of clinicians 130. The second plurality of clinicians 130 can be colocated at the same medical facility, affiliated with the same medical network, working in related fields, etc. In embodiments, the first plurality of clinicians and the second plurality of clinicians can have one or more clinicians in common. The further medical data is based on individual patient treatment outcomes 132 collected by the second plurality of clinicians. The patient treatment outcomes can include information regarding treatments tried, drug regimens prescribed, behavioral changes recommended, etc. The patient treatment outcomes can be based on medical data collected from a second plurality of patients. The second plurality of patients can be the patients served by the second plurality of clinicians. The second plurality of patients can be the patients served by the first plurality of clinicians. In embodiments, there can be overlap between the first plurality of patients and the second plurality of patients. One or more of the second plurality of patients can be patients served by both the first plurality of clinicians and the second plurality of clinicians, and so on. In other embodiments, there is no overlap between the first plurality of patients and the second plurality of patients.

The augmenting the medical knowledge database can be accomplished with a deep learning 134 system. The deep learning system can be based on a convolutional neural network (CNN) and other machine learning techniques. The deep learning system can be trained using collected medical data. The deep learning system can be trained using supervised learning, unsupervised learning, etc. In embodiments, the flow 100 further includes mapping a medical treatment to efficacy 136 using the deep learning system. The mapping of treatment to efficacy can include correlating treatment efficacy to patient demographic information, morphometric data and vital statistics, risk factors, etc. In embodiments, the flow 100 further includes determining an anticipated medical outcome 138 based on a medical treatment and a clinical state for the further patient. The anticipated medical outcome can include successfully treating a disease identified or considered likely based on a clinical state presented by the further patient. The anticipated medical outcome can include a percentage relating to a likelihood of success. In embodiments, the augmenting the medical knowledge database can be based on clinical states 140. One or more clinical states can be based on clinical findings. Clinical findings can include symptoms reported by a patient, objective signs observed by a clinician, disease prognosis, results of laboratory testing, and so on.

The flow 100 includes applying medical data from a further patient to the medical probabilistic rules graph that was augmented to produce a medical diagnosis 150. The medical data collected from the further patient can include demographic data, morphometric and vital statistics data, risk factors, previous diagnoses, and so on. In some embodiments, the further patient can be within the first plurality of patients or the second plurality of patients. In other embodiments, the further patient is distinct from the first plurality of patients and the second plurality of patients. The flow 100 further includes performing a query by a clinician 160 of the medical knowledge database. The query by the clinician can be performed through a dashboard, a graphical user interface (GUI), a web interface, an app, and so on. In embodiments, the query can be based on demographic data from an additional further patient. The demographic data from the additional further patient can include age, gender, race, ethnicity, education level, household income, geographic region, and so on. In embodiments, the query results in a diagnosis for the additional further patient. The diagnosis can include identifying a clinical state for the further patient. The diagnosis for the additional further patient can include a treatment plan. The treatment plan can include recommending coaching for behavioral changes such as smoking cessation, prescribing medications such as a statin to reduce cholesterol, and so on.

The flow 100 further includes projecting an impact for the further patient due to a change in medical treatment 170. The projecting an impact can include calculating, estimating, looking up, and otherwise determining a predicted impact to the patient. The impact can be calculated using deterministic rules, probabilistic rules, algorithms 172, procedures, code segments, apps, web apps, and so on. Other impacts for the patient can be determined. In embodiments, the flow 100 further includes projecting an impact due to a change in behavior. The change in behavior can include more than one change in behavior 174. The change in behavior can include smoking cessation, reducing or stopping the consumption of alcohol, losing weight, increasing exercise, reducing sodium intake, and so on. The impact that can be projected can include a change in risk level for the further patient. The change in risk level can include changes in developing medical states. The medical states can include heart disease, cancer, diabetes, kidney disease, liver disease, and so on. The change in risk level can include a change in absolute risk, a change in relative risk, and the like. The changes can include values such as a reduced LDL cholesterol number, a percentage risk change such as reducing the risk of cancer by smoking cessation, and so on.

The flow 100 further includes generating a treatment plan 180 for the further patient based on the medical probabilistic rules graph that was augmented. The treatment plan can include behavioral changes, drug regimens, counseling, surgeries, and so on. The treatment plan for the further patient can be further based on health background descriptors 182. Health background descriptors can include standard terms for describing histories such as family health history, patient medical history, etc. In embodiments, the health background descriptors can include ethnicity, age, gender, weight, height, body-mass index (BMI), smoking history, cholesterol levels, cholesterol ratio, medical history, blood pressure, family history, current drug treatments, previous drug treatments, alcohol consumption history, demographics, clinical state, and so on.

The medical knowledge database that is assembled is primarily evidence based. The data therein represents a compilation of factual studies, reports, medical observations, clinical trials, and the like, that go beyond the anecdotal data and occasional medical reports or best practices that are available to a human clinician. Millions of records can be distilled into the database and can require specialized software and or hardware to efficiently employ in a diagnosis process. In addition, evidence-based gaps can be identified in treatment plans and or medical care plans, which, by definition, are not apparent to a treating clinician. In embodiments, the medical diagnosis comprises a list of evidence-based treatments, lab work recommendations, diagnostic recommendations, or lifestyle interventions. In embodiments, the medical diagnosis provides evidence-based gaps in care or errors in treatment plans.

Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
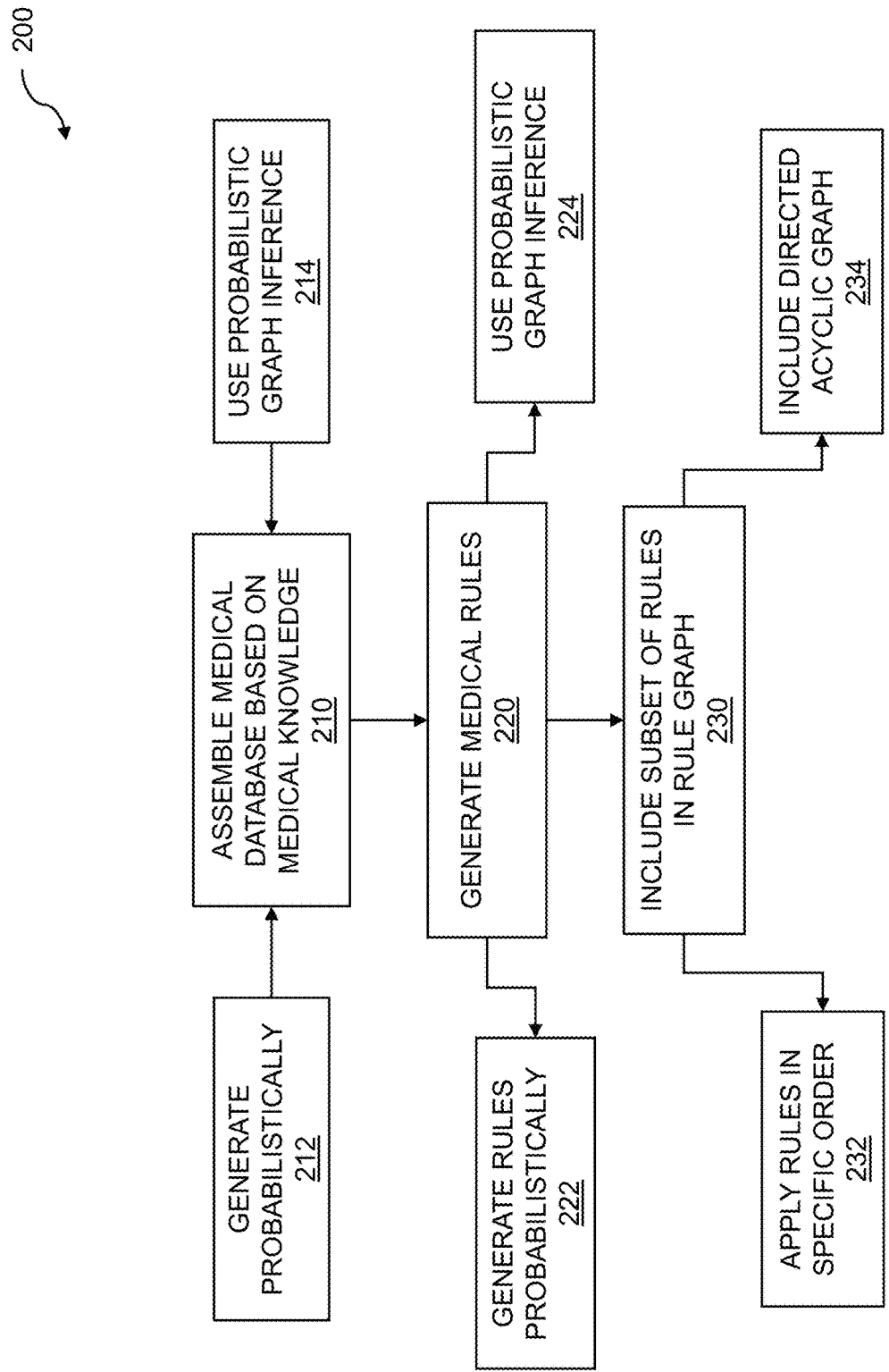
FIG. 2 is a flow diagram for assembling a medical database.

FIG. 2 is a flow diagram for assembling a medical database. A medical database can be assembled and used for machine learning for collaborative medical data metrics. Medical data is collected from clinicians serving patients and is used to assemble a medical knowledge database. The medical knowledge database is a function of demographics and includes a medical probabilistic rules graph. The medical knowledge database is augmented based on further medical data collected from a second group of clinicians. The medical data is based on individual patient treatment outcomes. The medical data from a further patient is applied to the medical probabilistic rules graph to produce a medical diagnosis. Impacts for the patient are projected based on changes in medical treatment, risk level, behavior, etc.

The flow 200 includes assembling a medical knowledge database 210 that includes medical knowledge information, medical diagnoses, and medical treatments, where the medical knowledge database is a function of demographics and comprises a medical probabilistic rules graph. The medical knowledge database can be stored on the device used for collecting, on a local server, on a remote server, on the distributed server, on a cloud server, and so on. In embodiments, the assembling the medical knowledge database can include generating medical rules based on the medical knowledge information. The medical rules can be applied to searches of the assembled medical knowledge database. The medical rules can include medical best practices. In embodiments, the medical rules can be generated probabilistically 212. The probabilities can include factors such as data previously loaded in the medical knowledge database, information relating to demographics, morphometric data and vital statistics, etc. Attributes can be applied to a medical rule. In embodiments, an output from the applying the attributes to the medical rule can be accomplished using a probabilistic graph inference 214.

The flow 200 includes generating medical rules 220 based on the medical knowledge information. As discussed previously, the medical rules that are generated can be used for searching the medical knowledge database to diagnose clinical states, prescribe treatment, and so on. The medical rules that are generated can include Boolean operations. In embodiments, the medical rules are generated probabilistically 222. Rules, such as rules for searching the medical knowledge database, can include probabilities for searching. The probabilities for searching can be based on demographic data, morphometric data, vital statistics, family history, and so on. The flow 200 can include using a probabilistic graph interface 224. The probabilistic graph can include a Bayesian network. The probabilistic graph interface can be used for accessing the probabilistic rules graph, visualizing the graph, for searching, for augmenting, and so on.

The flow 200 includes including a subset of the medical rules in the medical rules graph 230. The medical rules graph can be very large and complex because it can contain rules and probabilities for finding medical knowledge data, diagnosing medical conditions, determining treatments, recommending best practices, and so on. The medical rules graph can contain medical knowledge relating to many medical conditions, clinical states, and so on. In order to efficiently locate medical knowledge data relevant to a particular patient, the rules graph can be "pruned" to reduce search complexity. "Pruning" here refers to ignoring search paths with low probabilities of finding medical knowledge data relevant to the particular search. The including a subset of the medical rules can reduce a size of a search tree so that searching the medical knowledge database can be more efficient. The subset of the medical rules can be based on demographic data, morphometric data, patient historical data, and so on. In embodiments, the medical rules apply rules within the subset of the medical rules in a specific order 232 based on the ordering. Results of searching a database such as the medical knowledge database can be directly influenced by the queries issued to the database, and the order in which the queries can be issued. The medical rules can be applied in a specific order for search purposes, so that the search can be conducted efficiently, and so that the appropriate data can be located. The specific order can be used to accelerate the search, to improve accuracy of diagnosis, and so on. In embodiments, the medical rules graph includes a directed acyclic graph 234. A directed acyclic graph can include vertices and edges or arcs. The directed acyclic graph can describe medical knowledge data search steps, probabilities, weights, and so on, that can be used for a search.

Figure 3:
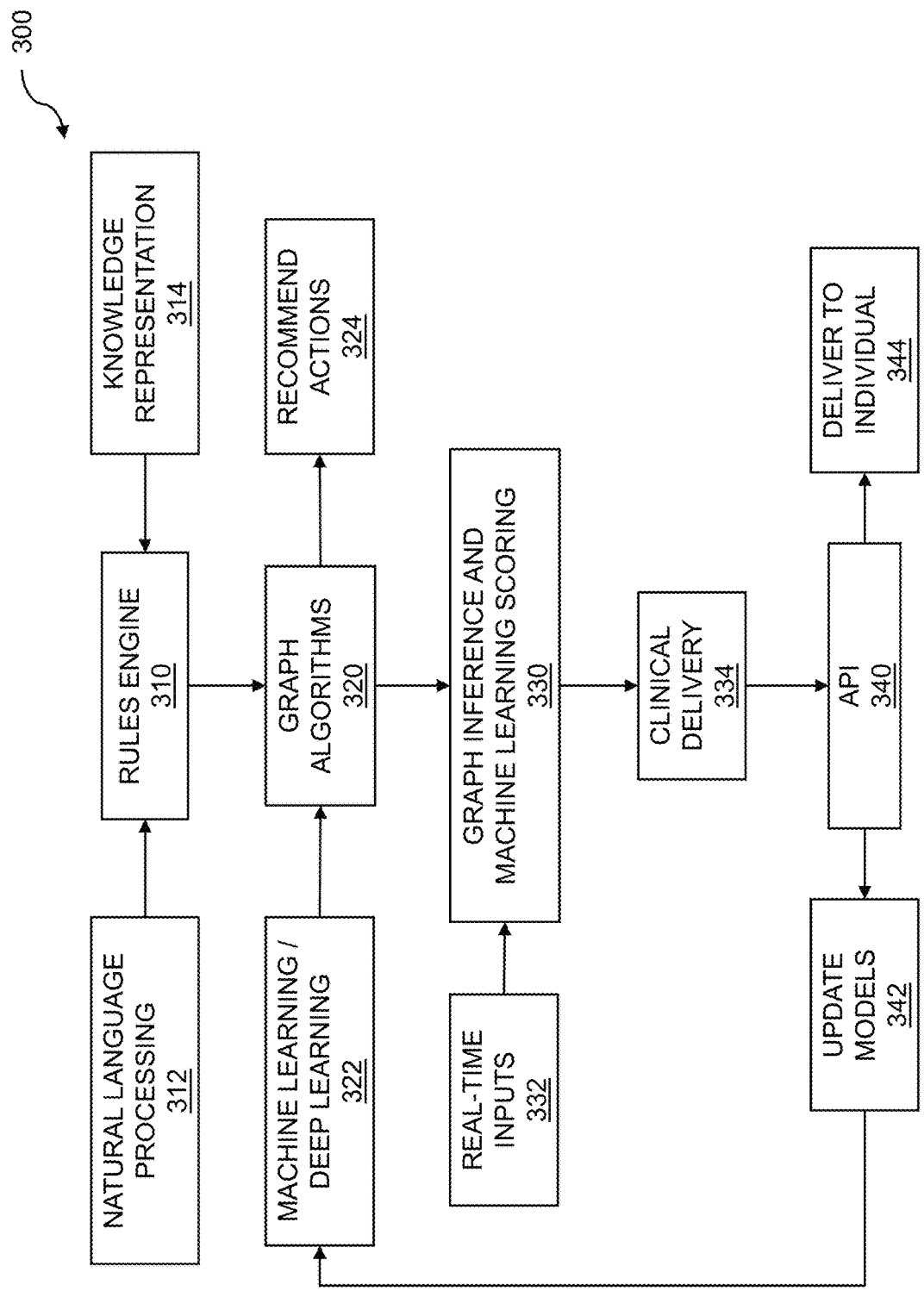
FIG. 3 is an architecture block diagram for medical analysis and learning.

FIG. 3 is an architecture block diagram for medical analysis and learning. The medical analysis and learning can be used for machine learning for collaborative medical data metrics. Medical data is collected from clinicians serving patients, and a medical knowledge database is assembled. The medical knowledge database includes medical knowledge information, medical diagnoses, and medical treatments. The medical knowledge database is a function of demographics and includes a medical probabilistic rules graph. The medical knowledge database is augmented based on further medical data collected from a second group of clinicians. The further medical data is based on individual patient treatment outcomes. Medical data from a further patient is applied to the medical probabilistic rules to produce a medical diagnosis. An impact for the patient is projected due to changing medical treatment, changing risk level, changing patient behavior, and so on.

The block diagram 300 includes a rules engine 310. The rules engine 310 takes a structured and consistent knowledge representation 314 of all available medical knowledge information and best practices. Natural language processing 312 can be used to process the knowledge representation 314 into medical rules through the rules engine 310. The rules from rules engine 310 are ordered into nodes and edges using one or more graph algorithms 320. The resulting graph is a medical probabilistic rule graph. The graph algorithms 320 can include recommending actions 324. The graph algorithms 320 can include machine learning/deep learning 322. The graph algorithms can order the medical knowledge data rules into a directed acyclic graph (DAG). The DAG can be ordered using graph inference and machine learning scoring 330. The graph can be customized by including real-time inputs 332, such as the attributes of an individual patient. The customized graph enables providing clinical delivery 334 of diagnoses and/or treatments through application programming interface (API) 340. The API 340 can be used to deliver diagnoses/treatments to an individual 344. API 340 can be used to update the models 342. The models can be updated by evaluating treatment results and feeding those results back into machine learning/deep learning 322 to update risk models and DAG nodes and edges. The models can be updated by adding desired clinical outcomes and feeding those outcomes back into the real-time inputs 332 to understand the relative probabilistic advantages of following clinical treatment recommendations, such as, for example, losing weight or continuing on an anti-hypertension drug. Feeding the updated models back through the machine learning/deep learning 322 into the graph algorithms 320 provides a valuable closed loop feedback path to actually improve the medical knowledge information and medical best practices captured by rules engine 310 and ordered algorithmically into a medical probabilistic directed acyclic rule graph.

In embodiments, the collecting, the augmenting, the applying, and the providing comprise machine learning medical analysis. Some embodiments comprise further augmenting the medical knowledge database based on non-medical data. Non-medical data refers to medical metadata or ancillary non-medical-condition-related data associated with a further patient. For example, a patient's health insurance situation may play a tremendous role in determining whether the patient will avail himself of a medically-recommended diagnostic procedure such as a colonoscopy. The simple questions of whether a patient's health care insurance deductible has been met, or whether a patient's insurer covers preventive care procedures with no out-of-pocket expense to the patient, can be deciding factors in establishing the actual course of action of the patient. Non-medical data is not generally available to the patient's clinician, but it can prove crucial in determining a treatment plan that will actually be implemented. Other examples of non-medical data include patient financial records, patient life events, work stresses, home living situation, socio-economic data, and societal relationships, to name just a few. Such non-medical data is distinct from any data available in clinical trials.

In addition, non-medical data such as demographics, while sometimes reported in clinical trials, can lead to gaps and errors in a diagnosis and/or treatment plan because an individual patient's critical demographic may not have been captured adequately in the clinical trial, but it may be captured accurately as distilled from millions of medical records used to build a medical knowledge database. Furthermore, the medical knowledge database may be used in somewhat of a "reverse operation" mode to suggest candidates for future clinical trials. For example, if a certain demographic has been underrepresented in diabetes clinical trials, the attending clinicians may be alerted to augment the trial's population of that underrepresented demographic. Thus, some embodiments further comprise applying further non-medical data from the further patient to the medical probabilistic rules graph, wherein the medical probabilistic rules graph has been updated based on the medical knowledge database that was further augmented.

The block diagram 300 can include providing information to and collecting information on, or from, an individual. The individual can be a patient. The delivery to an individual 344 can be made through an application programming interface (API) 340 and can include information on the ailment or the treatment, as well as actionable treatment goals. The ailment can include atherosclerotic cardiovascular disease (AS-CVD), insulin resistance, or breast cancer, to name but a few. The treatment can include statin therapy for ASCVD. The goals can include changing diet, reducing sodium intake, quitting smoking, and so on. The delivery to the individual 344 can include collecting therapeutic result information through API 340. The therapeutic result information can include biological information from the individual, where the biological information can be collected using a camera, sensors, a survey, and so on. In embodiments, the block diagram 300 can include providing feedback information to the medical practitioner. The feedback information to the medical practitioner can be through a first API 340, and the API supporting the delivery to the individual 344 can be through a second API. The feedback to the practitioner through API 340 can be in real-time. The feedback information can include the collected patient biological information, data from electronic medical records (EMR), data from clinical records (CR), etc. The block diagram 300 can include augmenting risk assessment, diagnosis, and treatment recommendations based on the medical knowledge information captured in the knowledge representation 314. The risk assessment can change based on how well the patient is meeting treatment goals and responding to treatment. Diagnoses can vary based on additional biological information that is collected from the patient, additional medical knowledge information, and so on. Treatment recommendations can be changed or can remain the same, depending on how the patient is responding to treatment, medical knowledge information, etc.

Various blocks in the block diagram 300 may be changed in order, repeated, omitted, or the like without departing from the disclosed concepts. Various embodiments of the block diagram 300 can be included in a computer program product embodied in a non-transitory computer readable medium that includes code executable by one or more processors. Various embodiments of the block diagram 300, or portions thereof, can be included on a semiconductor chip and implemented in special purpose logic, programmable logic, and so on.

Figure 4A:
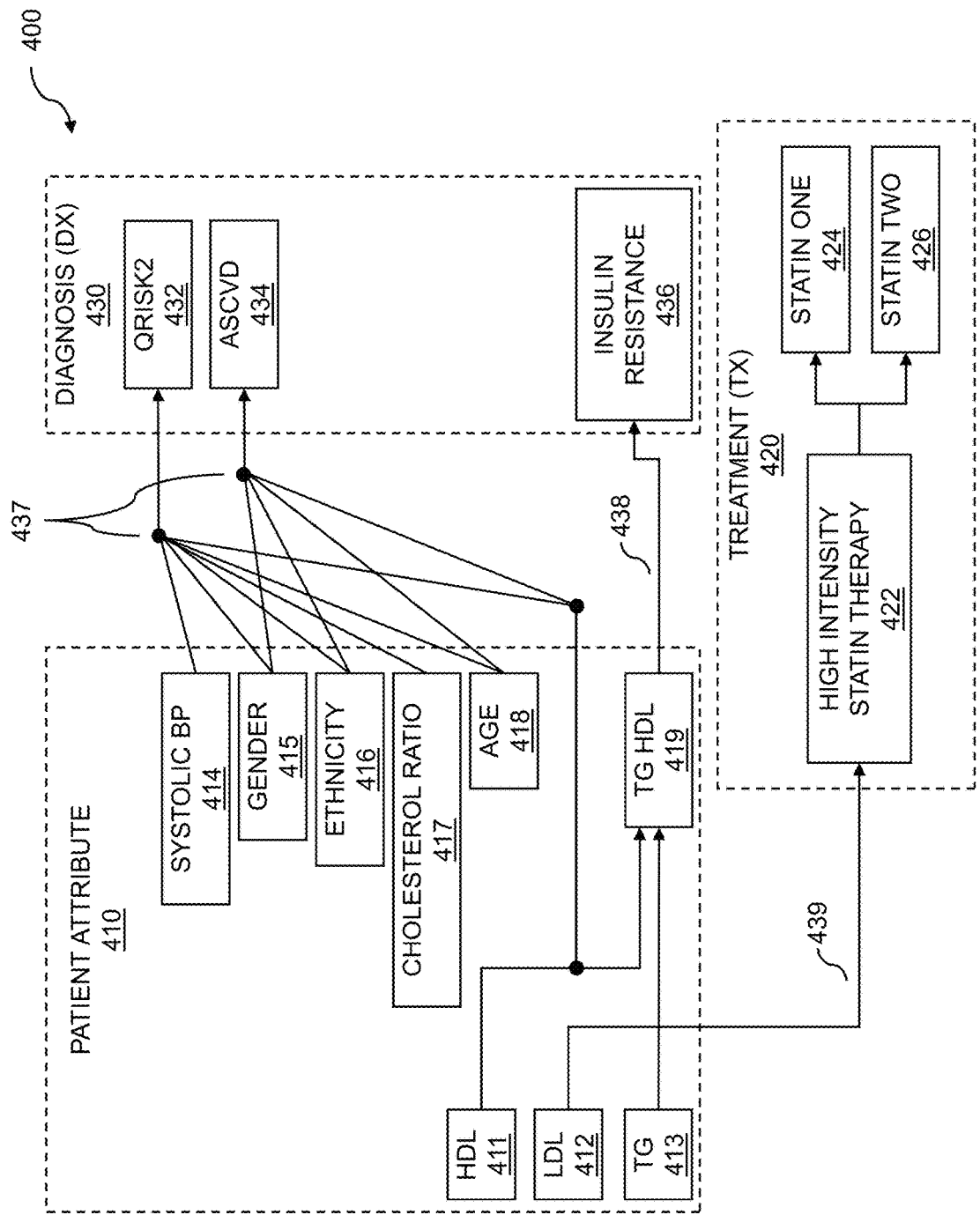
FIG. 4A illustrates medical analysis for diabetes.

FIG. 4A illustrates medical analysis for diabetes. Medical analysis and learning can be used for machine learning for collaborative medical data metrics. Medical data is collected from clinicians serving patients, and a medical knowledge database is assembled. The medical knowledge database is a function of demographics and includes a medical probabilistic rules graph. The medical knowledge database is augmented based on further medical data collected from a second group of clinicians. The medical data is based on individual patient treatment outcomes. The medical data from a further patient is applied to the medical probabilistic rules graph to produce a medical diagnosis. Impacts for the patient are projected based on changes in medical treatment, risk level, behavior, etc.

Illustration 400 shows an example of clinical intelligence for the care team. In the patient attribute section 410—grouped illustratively by a dashed line—an individual patient's salient attributes are summarized. The patient attribute section 410 can include patient attributes such as systolic blood pressure (BP) 414, gender 415, ethnicity 416, cholesterol ratio 417, and age 418. Other attributes can be included if they are salient to the current diagnosis, in this case, diabetes. Additional salient detail on cholesterol is provided such as high-density lipoproteins (HDL) 411, low-density lipoproteins (LDL) 412, and triglycerides (TG) 413. The HDL and TG can be combined into a single salient attribute TG HDL 419. The patient attributes enable individualized traversal of the nodes of the medical probabilistic rules graph.

Illustration 400 also includes a diagnosis (Dx) section 430, also grouped illustratively by a dashed line. The Dx 430 can include risk assessments based on applying the patient attributes to the medical probabilistic rule graph. Dx 430 includes the risk assessments QRISK2 432 and ASCVD 434, which are relative risks associated with diabetes. The risks can be referred to by arbitrary terms, such as QRISK2, or by actual acronym terms such as ASCVD, which stands for atherosclerotic cardiovascular diseases. These risk assessments, QRISK2 432 and ASCVD 434 are nodes in the medical probabilistic rule graph as traversed based on patient attributes, shown illustratively by various interrelated arrows 437. Dx 430 includes insulin resistance 436, which can be an important factor describing the patient's overall diagnosis and is predicated on the TG HDL 419 value as shown by arrow 438.

FIG. 4A includes an illustrated treatment (Tx) section 420, also grouped illustratively by a dashed line. Tx 420 includes high intensity statin therapy 422, which is the recommended treatment based on the application of patient attributes to the medical probabilistic rule graph. In particular, patient LDL 412 is shown to be an important factor in the treatment recommendation, indicated by arrow 439. In addition, based on the current and best medical information data, two specific drugs are indicated, namely statin drug one 424 and statin drug two 426. The medical analysis and learning for diabetes process illustrated in FIG. 4A, or portions thereof, can be implemented using a mobile device, a server, a web interface into a cloud processor, and so on. The illustration 400, or portions thereof, can be implemented using one or more processors. The illustration 400 shows a self-learning clinical intelligence system based on biological information and medical knowledge information.

Figure 4B:
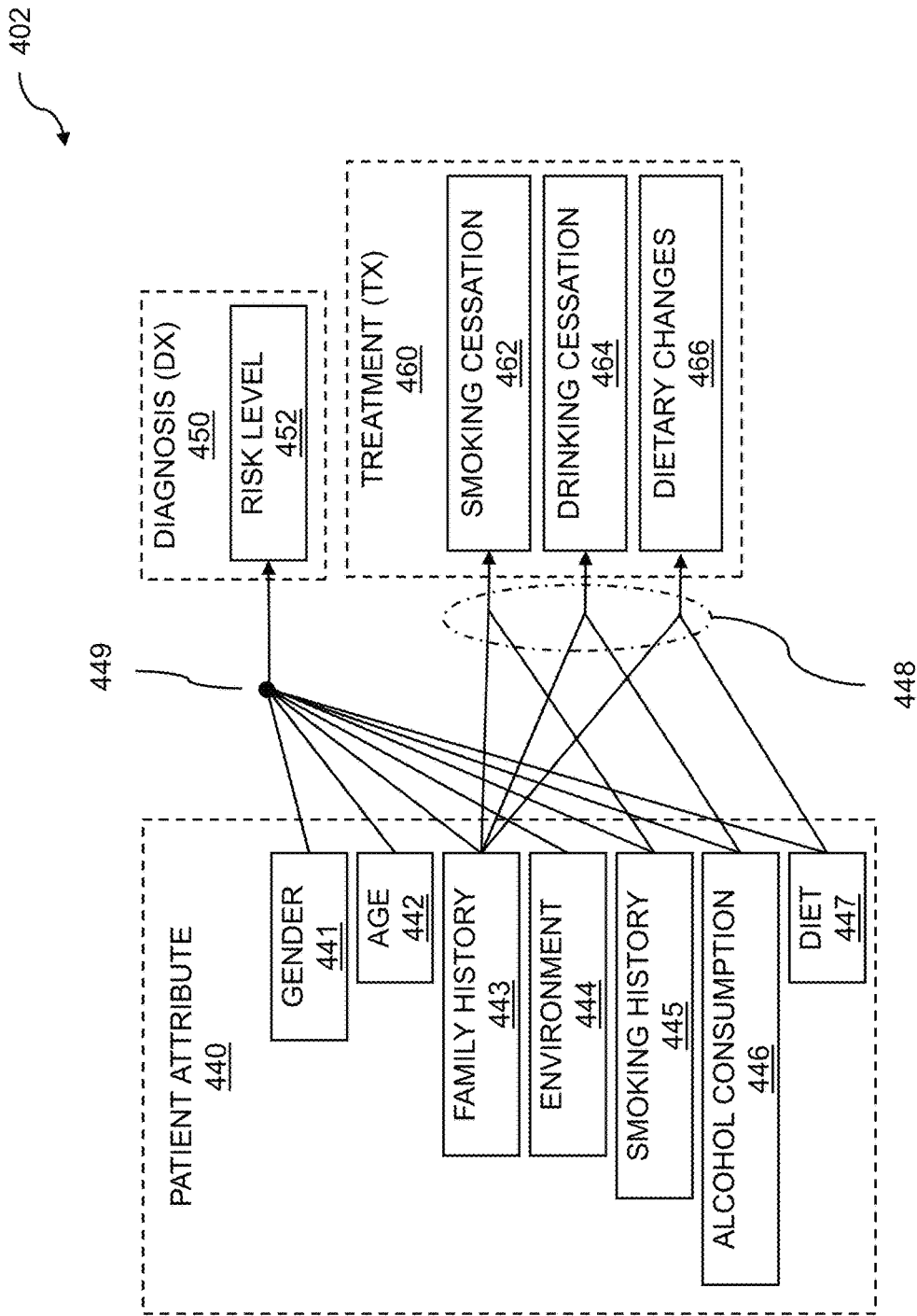
FIG. 4B illustrates medical analysis for heart disease risk.

FIG. 4B illustrates medical analysis for heart disease risk. Medical analysis and learning can be used for machine learning for collaborative medical data metrics. Illustration 402 shows another example of clinical intelligence for the care team. In the patient attribute section 440—grouped illustratively by a dashed line—an individual patient's salient attributes are summarized for heart disease risk evaluation. The patient attributes 440 can include gender 441, age 442, family history 443, environment 444, smoking history 445, alcohol consumption 446, and diet 447. Other attributes can be included if they are salient to the current diagnosis, in this case, heart disease risk. The patient attributes enable individualized traversal of the nodes of the medical probabilistic rules graph.

Illustration 402 also includes a diagnosis (Dx) section 450, also grouped illustratively by a dashed line. The Dx 450 can include risk level assessments based on applying the patient attributes to the medical probabilistic rule graph. The risk level assessment, risk level 452, is based on traversing the nodes in the medical probabilistic rule graph based on patient attributes, shown illustratively by various interrelated arrows 449.

FIG. 4B includes an illustrated treatment (Tx) section 460, also grouped illustratively by a dashed line. Tx 460 includes smoking cessation 462, drinking cessation 464, and dietary changes 466, as illustrated by arrows 448. The medical analysis and learning for diabetes process illustrated in FIG. 4B, or portions thereof, can be implemented using a mobile device, a server, a web interface into a cloud processor, and so on. The illustration 402, or portions thereof, can be implemented using one or more processors. The illustration 402 shows a self-learning clinical intelligence system based on biological information and medical knowledge information.

Figure 4C:
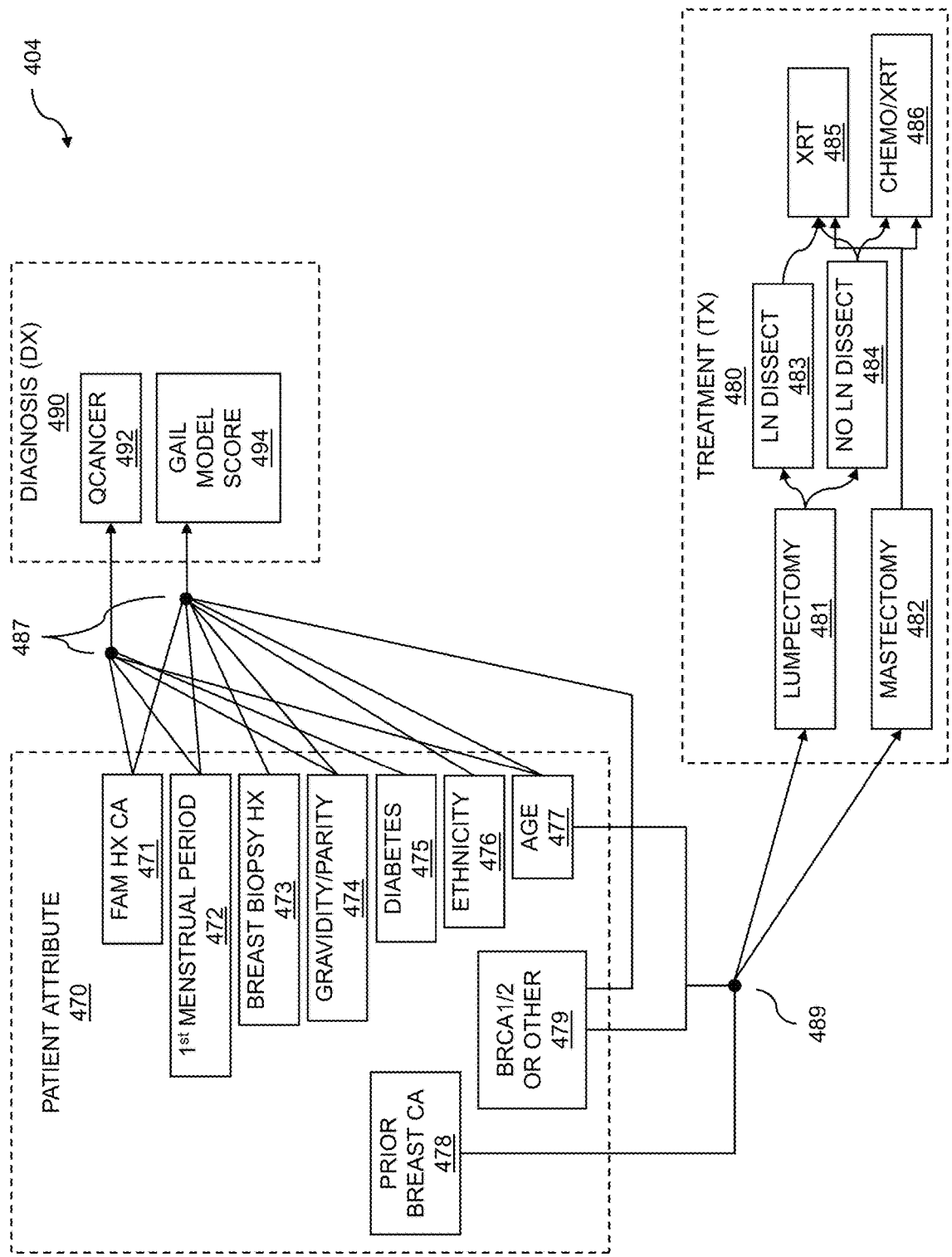
FIG. 4C illustrates medical analysis for breast cancer.

FIG. 4C illustrates medical analysis for breast cancer. Medical analysis and learning can be used for machine learning for collaborative medical data metrics. Illustration 404 shows an example of clinical intelligence for the care team. In the patient attribute section 470—grouped illustratively by a dashed line—an individual patient's salient attributes are summarized. The patient attributes 470 can include a family history of cancer (FAM Hx CA) 471, age of first menstrual period 472, breast biopsy history (Hx) 473, gravidity/parity 474 (obstetrical history), diabetes 475, ethnicity 476, and age 477. Other attributes can be included if they are salient to the current diagnosis, in this case, breast cancer risk. Additional salient detail on the presence of certain gene mutations is included such as BRCA1 and BRCA2 or other cancer-related mutations. Additional salient detail such as a history of prior breast cancer (CA) 478 is included. The patient attributes enable individualized traversal of the nodes of the medical probabilistic rules graph.

Illustration 404 includes a diagnosis (Dx) section 490, also grouped illustratively by a dashed line. The Dx 490 can include risk assessments of breast cancer based on applying the patient attributes to the medical probabilistic rule graph. Dx 490 includes the risk assessments QCANCER 492 and Gail Model score 494, which are relative risks associated with breast cancer. The risks can be referred to by arbitrary terms, such as QCANCER, or by actual industry terms such as the Gail Model score for breast cancer risk assessment. These risk assessments, QCANCER 492 and Gail Model score 494, are nodes in the medical probabilistic rule graph as traversed based on patient attributes, shown illustratively by various interrelated arrows 487.

FIG. 4C includes an illustrated treatment (Tx) section 480, also grouped illustratively by a dashed line. Tx 480 includes a lumpectomy 481 and a mastectomy 482, which are the recommended treatments based on the application of patient attributes to the medical probabilistic rule graph. In particular, lumpectomy 481 and mastectomy 482 can be indicated by prior breast CA 478, BRCA1/2 or other mutations 479, and patient age 477, as shown by arrow 489. The lumpectomy 481 can include or exclude the dissection of lymph nodes (LN). LN dissection 483 results, or no LN dissection 484, can indicate radiation therapy (XRT) 485 or chemotherapy and XRT 486. Likewise, mastectomy 482 can indicate XRT 485 or chemo/XRT 486. The medical analysis and learning for breast cancer process illustrated in FIG. 4C, or portions thereof, can be implemented using a mobile device, a server, a web interface into a cloud processor, and so on. The illustration 404, or portions thereof, can be implemented using one or more processors. The illustration 404 shows a self-learning clinical intelligence system based on biological information and medical knowledge information.

Figure 5:
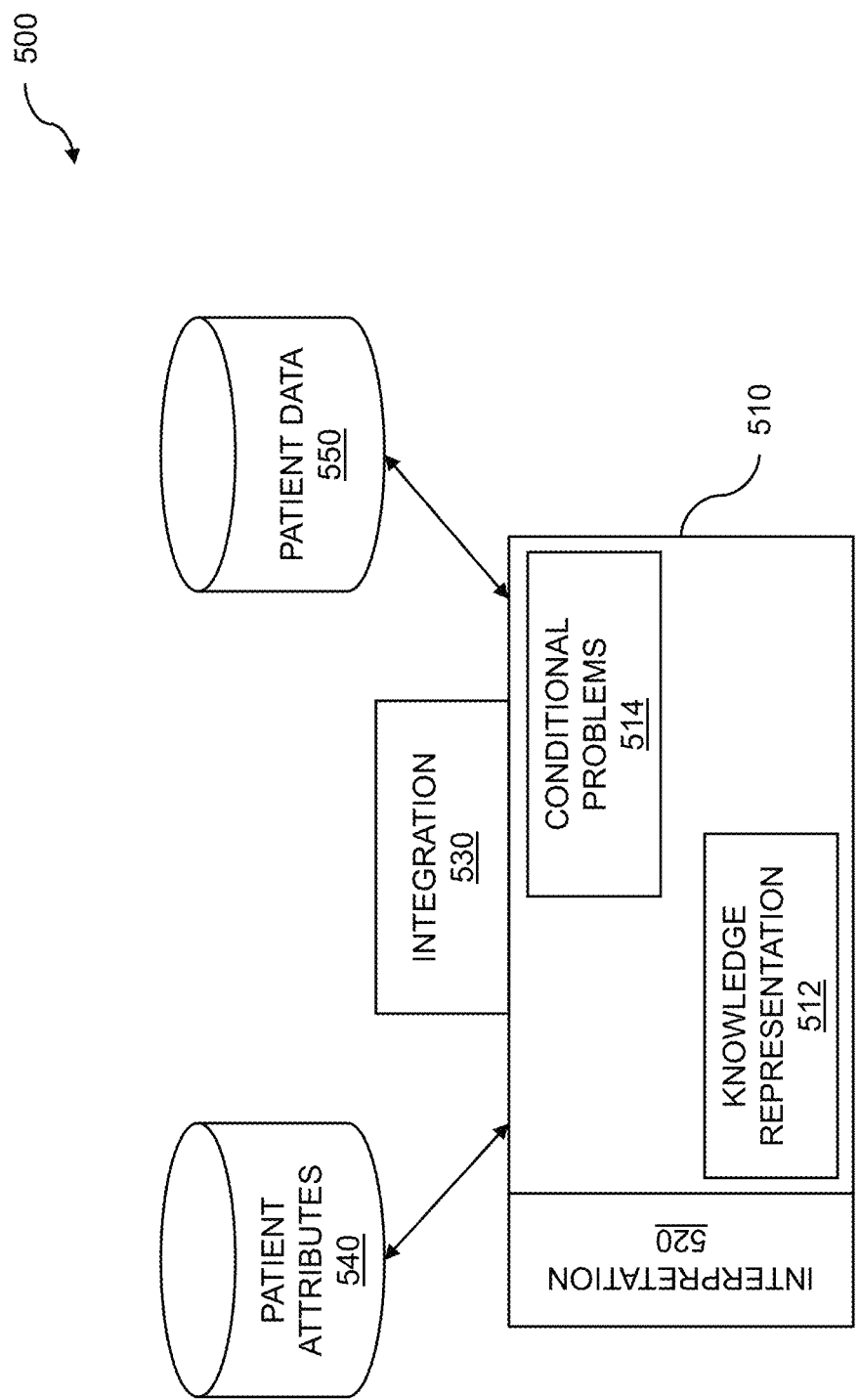
FIG. 5 shows patient knowledge representation and rule application.

FIG. 5 shows patient knowledge representation and rule application. The patient knowledge representation and rule application can be used for machine learning for collaborative medical data metrics. Medical data is collected from clinicians serving patients, and a medical knowledge database is assembled. The medical knowledge database includes medical knowledge information, medical diagnoses, and medical treatments. The medical knowledge database is a function of demographics and includes a medical probabilistic rules graph. The medical knowledge database is augmented based on further medical data collected from a second group of clinicians. The further medical data is based on individual patient treatment outcomes. Medical data from a further patient is applied to the medical probabilistic rules to produce a medical diagnosis. An impact for the patient is projected due to changing medical treatment, changing risk level, changing patient behavior, and so on.

Patient knowledge representation and rule application 500 can be included in a self-learning clinical intelligence system. The self-learning clinical intelligence system can be based on biological information and medical knowledge information. The self-learning clinical intelligence system can include obtaining medical metrics, receiving biological information and other information from an individual, and applying the medical metrics to the biological information from the individual. The medical metrics can be applied to the biological information from the individual to diagnose an ailment, recommend a treatment, and so on. Knowledge representation and rule application 500 can include a knowledgebase 510. The knowledgebase 510 can include various types of data including medical knowledge information, biological information from an individual, clinical data, and so on. The knowledgebase can include knowledge representation 512 where the knowledge representation can describe how the various types of data can be stored in the knowledgebase, such as using tuples. The knowledgebase 510 can include conditional problems 514, which can be used to describe how to analyze the data stored in the knowledgebase. The information and data stored in the knowledgebase can undergo interpretation 520. The interpretation can be based on medical taxonomies and ontologies. Interpretation can be used to diagnose an ailment, recommend a treatment, and so on. Input data can be received from electronic medical records (EMR), clinical records (CR), and so on. The interpretation can be used to process the input data and to render output data. The output data can include diagnoses, treatments, etc. The information and data stored in the knowledgebase can be integrated 530. The integration can include integration of data from various sources such as EMR, CR, etc., and can include data normalization. Patient data 550 can be obtained for input to and storage from the knowledgebase 510. Patient data can include biological data, EMR, CR, and so on. Patient attributes 540 can be obtained for input to and storage from the knowledgebase 510. Patient attributes can include gender, age, ethnicity, family history, etc.

Figure 6:
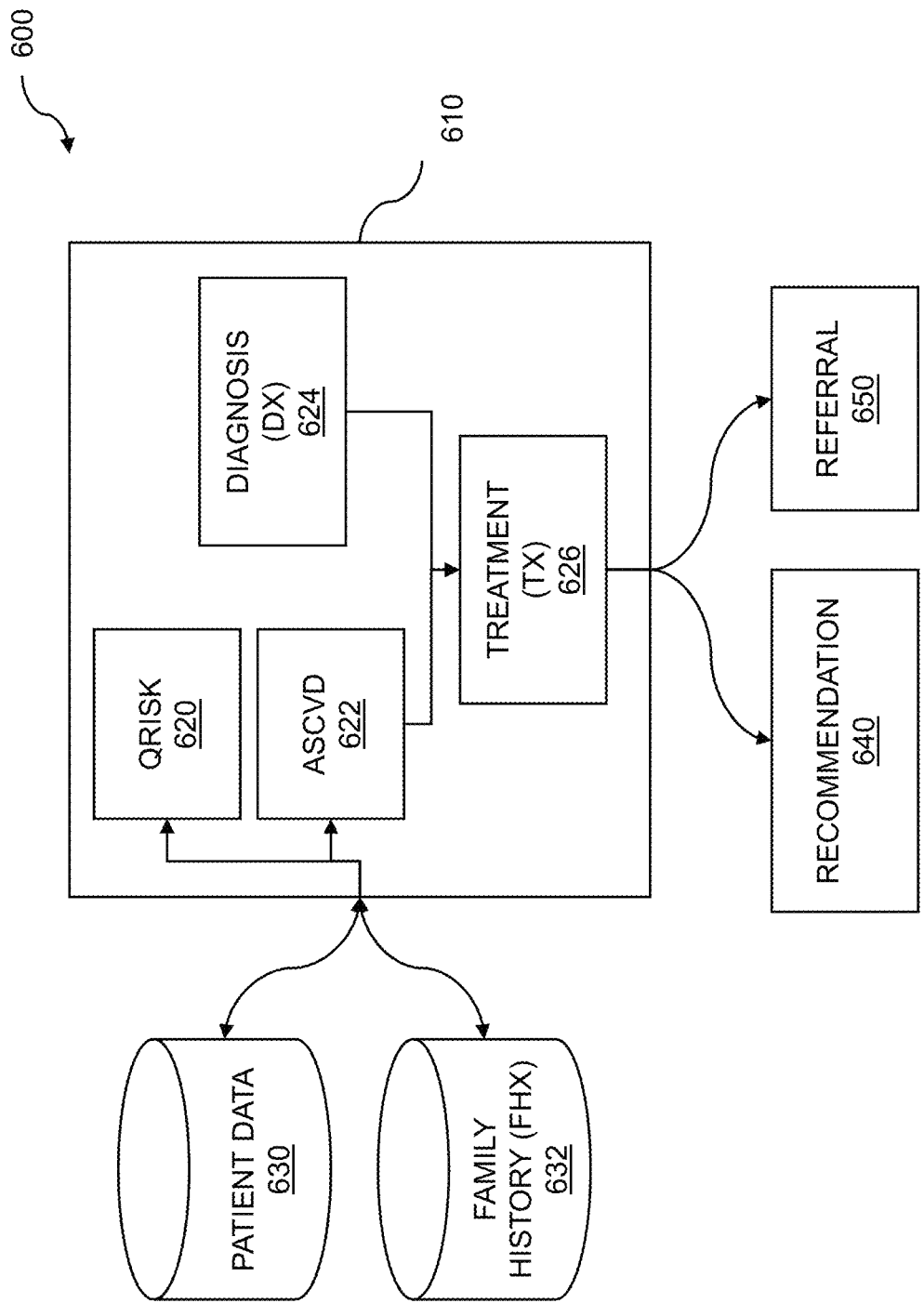
FIG. 6 shows diagnosis and treatment interactions for ASCVD.

FIG. 6 shows diagnosis and treatment interactions for ASCVD. Diagnosis and treatment interactions 600 for various conditions including ASCVD can be included in a system for machine learning for collaborative medical data metrics. Medical data is collected from clinicians serving patients, and a medical knowledge database is assembled. The medical knowledge database is a function of demographics and includes a medical probabilistic rules graph. The medical knowledge database is augmented based on further medical data collected from a second group of clinicians. The medical data is based on individual patient treatment outcomes. The medical data from a further patient is applied to the medical probabilistic rules graph to produce a medical diagnosis. Impacts for the patient are projected based on changes in medical treatment, risk level, behavior, etc.

Diagnosis and treatment interactions for ASCVD can include an analyzer 610 that can analyze medical and biological data. The data can include patient data 630, where the patient data can be stored in multiple databases such as patient electronic medical records (EMR), clinical records, third party records, and so on. The data can include family history data (FHx) 632, where the family history data can be stored in multiple databases, and where the family history data can include such family medical history as occurrences of coronary heart disease, cancer, and other health ailments. The analyzer 610 can consider health risk assessment techniques such as QRISK 620, a prediction algorithm for cardiovascular disease (CVD), and ASCVD 622. A diagnosis (Dx) 624 for an ailment can be provided. The diagnosis 624 can be based on risk factors, aggregate risk assessments, and so on. Error analysis can be conducted, where the error analysis can be based on determining confidence intervals. The confidence intervals can be related to the contributions of individual risk factors to the aggregate risk factor. Error analysis for each risk can be based on the confidence interval of a risk score, a confusion matrix, and other factors including measurement precision and accuracy, recall, receiver operating characteristic (ROC), and so on. The analysis results from QRISK and ASCVD, and the diagnosis, can be used to determine a treatment (Tx) 626. The results of determining a treatment can include making one or more recommendations 640 to the patient and/or medical practitioner, and making a referral 650.

Figure 7:
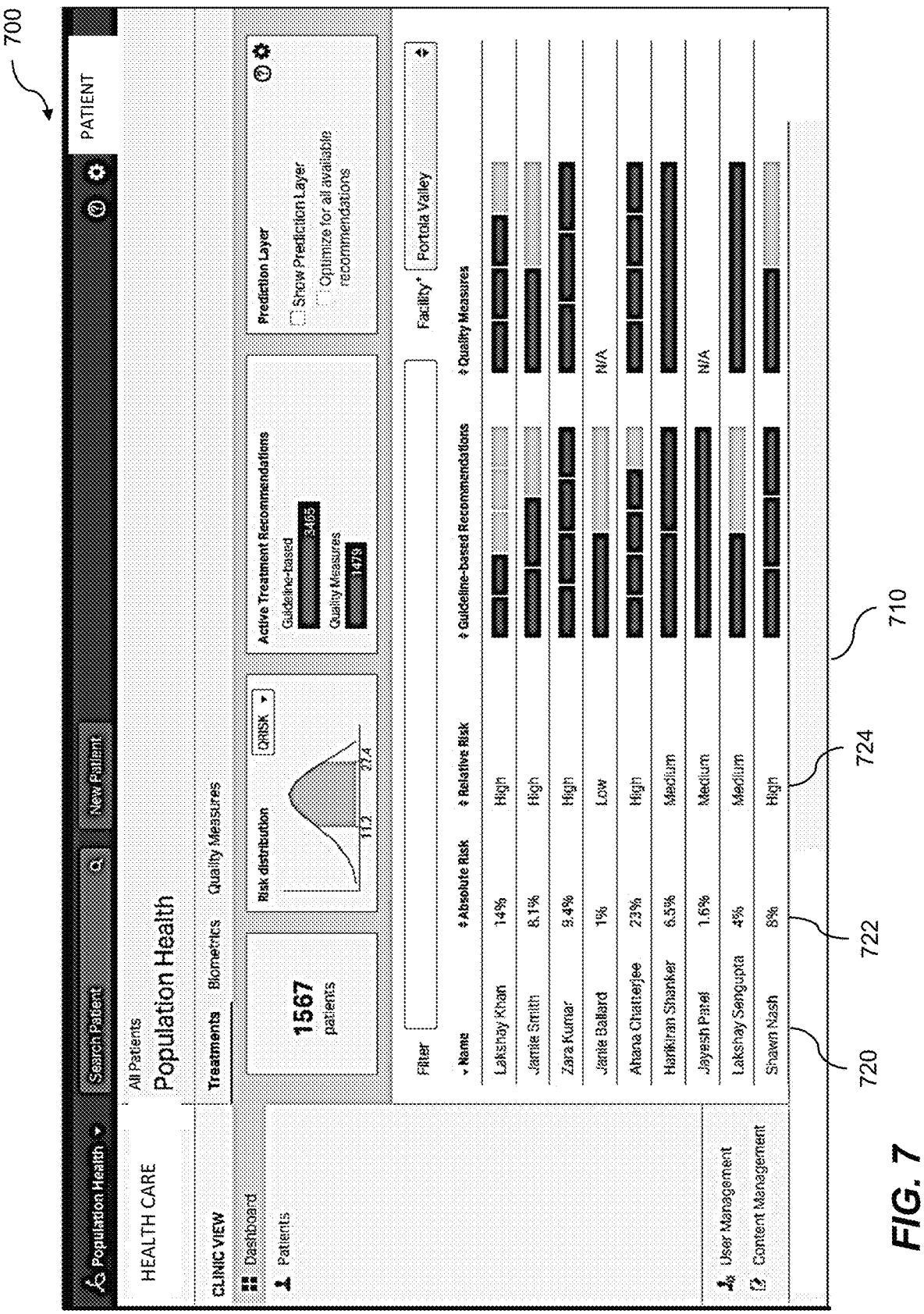
FIG. 7 shows an example of population health.

FIG. 7 shows an example of population health. Population health can include data related to diseases, health conditions, and so on, across of a population of patients. Population health can include further data such as demographic data, medical history, family medical history, etc. Population health can be rendered and displayed for machine learning for collaborative medical data metrics. Medical data is collected from clinicians serving patients, and a medical knowledge database is assembled. The medical knowledge database includes medical knowledge information, medical diagnoses, and medical treatments. The medical knowledge database is a function of demographics and includes a medical probabilistic rules graph. The medical knowledge database is augmented based on further medical data collected from a second group of clinicians. The further medical data is based on individual patient treatment outcomes. Medical data from a further patient is applied to the medical probabilistic rules to produce a medical diagnosis. An impact for the patient is projected due to changing medical treatment, changing risk level, changing patient behavior, and so on.

An example 700 of population health is shown. The population health can be rendered as a visual representation such as a dashboard and displayed on a screen 710. The screen 710 can be any digital screen including a screen coupled to device such as a smartphone, tablet, personal digital assistant (PDA), laptop computer or other computer, and so on. Various types of information, including information relating to public health, can be displayed on the dashboard. The various types of information can include a number representing total patients, a listing of patients by name 720, an absolute risk 722, a relative risk 724, risk distribution, active treatment recommendations, guideline-based recommendations, quality measures, and so on. Relative risk can be described by a value, a range of values, a percentage, a threshold, a relative value or description, etc. Relative risk can include factors such as patient health history, family history, lifestyle, other patient diseases or conditions, and so on. The patients can be included within a plurality of patients, as discussed throughout. The patients can be included in the first plurality of patients, the second plurality of patients, both pluralities of patients, etc. A patient, such as the further patient, can be displayed. Other patients and their information can be displayed. Various features and displays can be selected through the dashboard.

FIG. 8 illustrates an example of ethnicity and risk factors. Data can be sorted, analyzed, rendered, displayed, etc., based on variety of parameters. The parameters can include disease or condition, population, demographic data, and so on. An ethnicity parameter can be used to sort, analyze, etc. population health data. Ethnicity can be associated with risk factors. Ethnicity and risk factors can be rendered and displayed for machine learning for collaborative medical data metrics. Medical data is collected from clinicians serving patients, and a medical knowledge database is assembled. The medical knowledge database is a function of demographics and includes a medical probabilistic rules graph. The medical knowledge database is augmented based on further medical data collected from a second group of clinicians. The medical data is based on individual patient treatment outcomes. The medical data from a further patient is applied to the medical probabilistic rules graph to produce a medical diagnosis. Impacts for the patient are projected based on changes in medical treatment, risk level, behavior, etc.

An example 800 of ethnicity and risk factors is shown. The ethnicity and risk factors data can be rendered as a dashboard and displayed on an electronic display 810. The electronic display can include a display coupled to an electronic device such as a smartphone, PDA, tablet computer or other computer, etc. The ethnicity and risk factors dashboard can include population health data such as patient names, ethnicities corresponding to the patient names, and so on. The ethnicity and risk factors dashboard can include other measures or data. The measures can include risk type, body mass index (BMI), blood pressure, cholesterol ratio, low-density lipoprotein (LDL) value, LDL particle count, lipoprotein(a) (Lp(a)), APO B, and so on. A given risk factor and measure or data can be represented by a value, a percentage, a ratio, a scale, and so on. The risk factors and measures can be evaluated and ranked. The ranking can be based on a threshold, a value, a percentage, a ratio, and so on. The ranks of risk factors and measures can be rendered and displayed. In embodiments, the risk factors and measures can include a visual indicator. The visual indicator can include a green rendering to signify a "good" rate, a yellow rendering to signify an "OK" or "caution" rate, and red rendering to signify a "bad" rate. In the example 800, a "bad" rate is indicated by a value within bold outline 820, an "OK" rate is indicated by a value in italics 822, and a good rate is indicated by plain text. The ranks of risk factors and measures can be used by clinicians or other medical professionals to recommend to patients changes in lifestyle, drug therapies, counseling, and so on.

Figure 9:
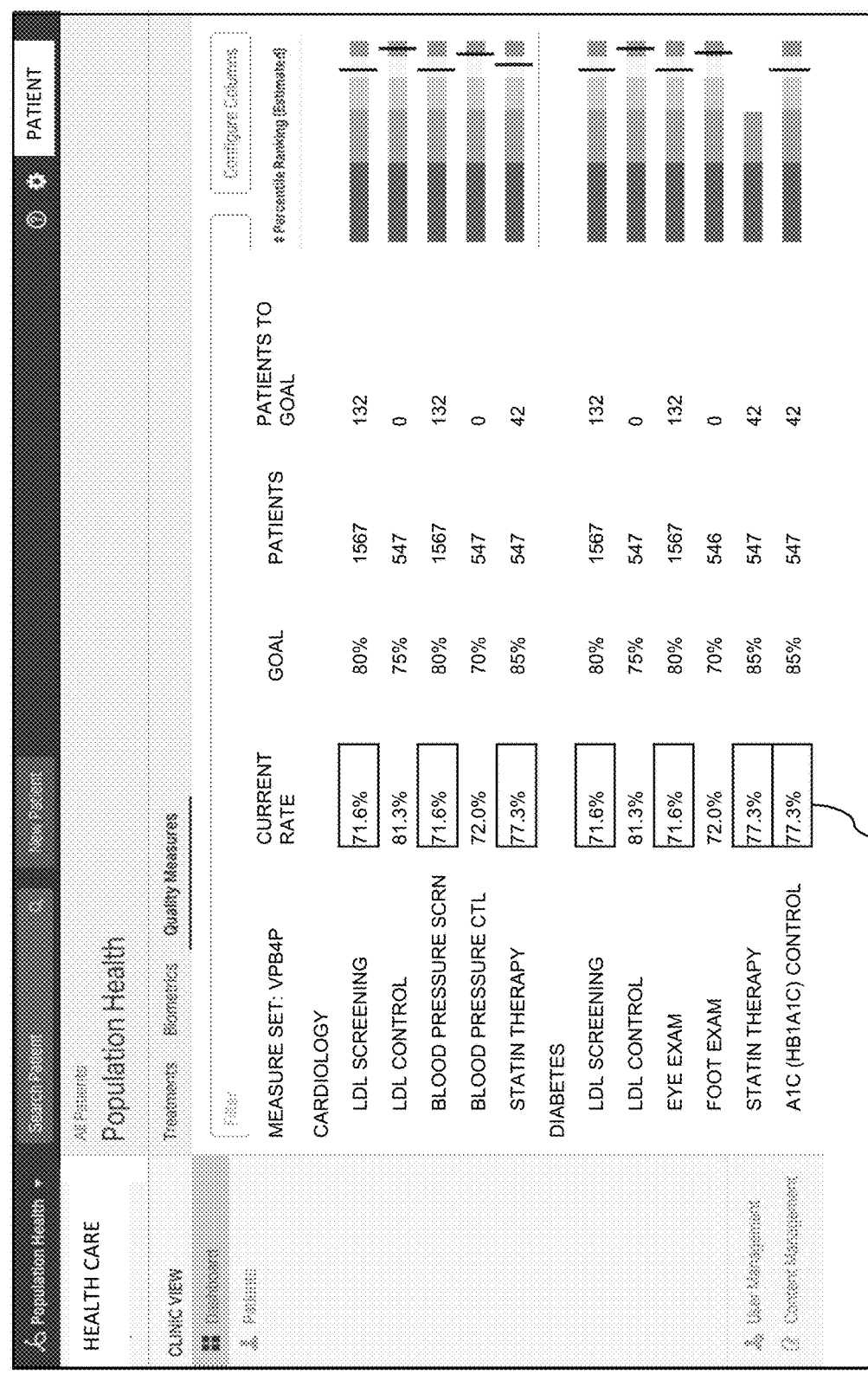
FIG. 9 is an example of quality measures.

FIG. 9 is an example of quality measures. Quality measures can be applied to a health population, where a health population can include one or more patients. The quality measures can be viewed based on treatments that can be applied for various diseases or conditions, biometric data, quality measures and so on. The quality measures can be rendered and displayed for machine learning for collaborative medical data metrics. Medical data is collected from clinicians serving patients, and a medical knowledge database is assembled. The medical knowledge database includes medical knowledge information, medical diagnoses, and medical treatments. The medical knowledge database is a function of demographics and includes a medical probabilistic rules graph. The medical knowledge database is augmented based on further medical data collected from a second group of clinicians. The further medical data is based on individual patient treatment outcomes. Medical data from a further patient is applied to the medical probabilistic rules to produce a medical diagnosis. An impact for the patient is projected due to changing medical treatment, changing risk level, changing patient behavior, and so on.

An example 900 of quality measures is shown. The quality measures, as well as other factors or parameters such as treatments or biometrics, can be rendered to display population health data. The population health data, such as the quality measures data, can be rendered as a dashboard 910. The dashboard can be displayed on an electronic display including a display coupled to an electronic device. The electronic device to which the display is coupled can include a smartphone, a personal digital assistant, a tablet computer, a laptop computer, and the like. The quality measures dashboard can include various health categories, disease types, etc. The health categories can include cardiology. Cardiological information can include data collected from a population of patients, where the information can be analyzed, averaged, measured against a threshold, and so on. The cardiological information and include data for LDL screening, LDL control, blood pressure screening, blood pressure control, statin therapy, and so on. The categories can include diseases such as cancer, liver disease, kidney disease, diabetes, etc. The disease categories can include diabetes. The diabetes category can include data such as LDL screening, LDL control, eye exam, foot exam, statin therapy, A1C (Hb 1A1C) control, and so on.

The dashboard for quality measures can be rendered, where the quality measures can include data obtained from the population of patients. The patient population data can include data such as current rate, a percent goal, a number of patients, a patients-to-goal rating, a percentile ranking, and so on. The category and quality measures dashboard can include a visual indicator such as green to signify a "good" rate, yellow to signify an "OK" or "caution" rate, red to signify a "bad" rate, etc. In the example 900, "bad" rates are designated with a bold outline such as 920, while "good" rates are not so designated. The visual indicators or "good", "ok", or "bad" can quickly convey to clinicians or other health care providers quality measures that are subpar and may require further attention or action. Further action can include recommending lifestyle changes, prescribing drug therapies such as statin therapies, and the like.

Figure 10:
FIG. 10 illustrates an example of recommendations and treatment plans.

FIG. 10 illustrates an example of recommendations and treatment plans. Recommendations and treatment plans can be determined or proposed for a patient based on data related to the patient. Patient data can be analyzed or compared based on information within one or more medical databases. The recommendations and treatment plans can be rendered and displayed for machine learning for collaborative medical data metrics. Medical data is collected from clinicians serving patients, and a medical knowledge database is assembled. The medical knowledge database is a function of demographics and includes a medical probabilistic rules graph. The medical knowledge database is augmented based on further medical data collected from a second group of clinicians. The medical data is based on individual patient treatment outcomes. The medical data from a further patient is applied to the medical probabilistic rules graph to produce a medical diagnosis. Impacts for the patient are projected based on changes in medical treatment, risk level, behavior, etc.

An example 1000 is shown for recommendations and treatment plans. Recommendations can be made and treatment plans determined for a patient, where the recommendations and determinations are based on information relating to the patient and on accessing knowledge sources including medical knowledge sources. The knowledge sources for the recommendations and treatment plans can be shown. The knowledge sources, recommendations, and treatment plan data can be rendered as a dashboard. The dashboard can be displayed to the patient, a physician or clinician, a health care provider, and so on. The dashboard can be displayed on an electronic display 1010. The electronic display can include a display coupled to an electronic device such as a smartphone, a tablet, a laptop computer or other computer, and so on. The recommendations and treatment plans dashboard as rendered on the electronic display can include patient data 1020. The patient data can include a patient name and a patient summary. The patient summary can include the name of a patient along with her or his demographic data, morphometric data and vital statistic information, risk factors and diagnoses, etc. The demographic data can include age, gender, ethnicity, etc. Vital statistic information can include morphometric and vital information such as blood pressure, weight, height, BMI, etc. Risk factors can include smoking history, family cardiovascular disease (CVD), family cancer instance, chronic renal disease, atrial fibrillation, diabetes, etc.

The electronic display 1010 dashboard can include recommendations 1022. Recommendations can include changes in behavior such as smoking cessation, weight loss, or exercise; drug therapy such as prescribing statins or antihypertensive drugs, etc. The recommendations can be ranked or prioritized based on various types of risks or other factors such as patient history. The ranking can be determined based on contributions associated with a given risk or predictor of risk such as QRISK2. The dashboard 1000 can include designing a treatment plan 1024. The designing a treatment plan can include making referrals to lifestyle change programs such as receiving coaching for tobacco cessation, meeting with a dietician, or arranging a fitness consultation with a personal trainer. The treatment plan can include prescribing drug therapy. The prescribing drug therapy can include prescribing drug types, dosage amounts and frequencies, etc.

Figure 11:
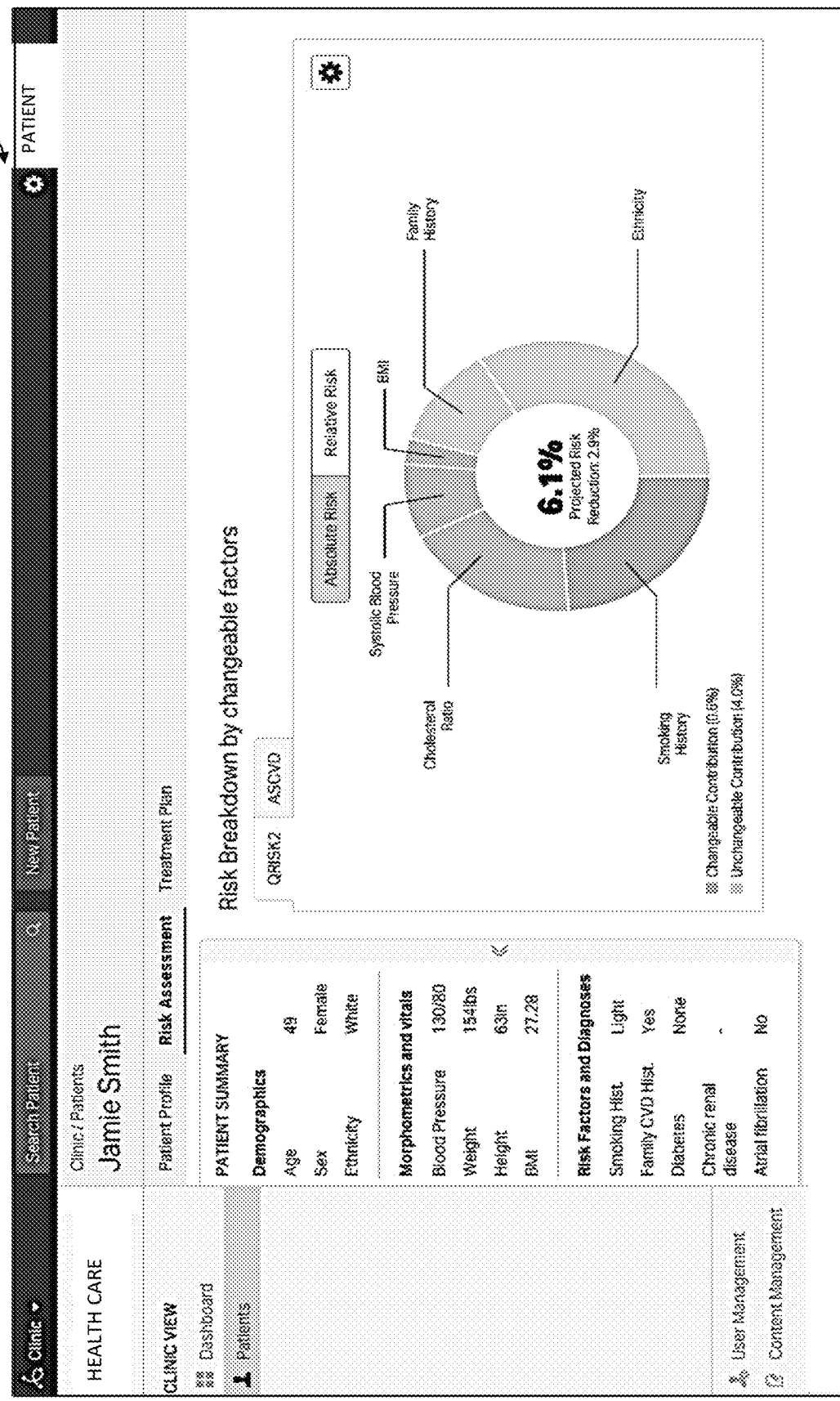
FIG. 11 shows an example of risk breakdown by changeable factors.

FIG. 11 shows an example of risk breakdown by changeable factors. The risk of a patient can be characterized or "broken down" by risk factors that can be changed. Changeable risk factors can include weight reduction, exercise regimens, smoking cessation, alcohol consumption reduction or elimination, avoiding risky behaviors, reducing or eliminating environmental factors, and so on. Risk breakdown by changeable factors can be rendered and displayed for machine learning for collaborative medical data metrics. Medical data is collected from clinicians serving patients, and a medical knowledge database is assembled. The medical knowledge database includes medical knowledge information, medical diagnoses, and medical treatments. The medical knowledge database is a function of demographics and includes a medical probabilistic rules graph. The medical knowledge database is augmented based on further medical data collected from a second group of clinicians. The further medical data is based on individual patient treatment outcomes. Medical data from a further patient is applied to the medical probabilistic rules to produce a medical diagnosis. An impact for the patient is projected due to changing medical treatment, changing risk level, changing patient behavior, and so on.

An example 1100 is shown for risk breakdown by changeable factors. The risk breakdown by changeable factors can include patient information and a graphical rendering for risk breakdown. The patient information and the risk breakdown graphics can be rendered as a dashboard and displayed on an electronic display 1110. The electronic display can include a display coupled to an electronic device such as a tablet, smartphone, PDA, laptop, etc. The risk breakdown and changeable factors dashboard can include the name of a patient along with her or his demographic data, morphometric and vital statistic information, risk factors, etc. The demographic data can include age, gender, ethnicity, etc. Morphometric and vital statistic information can include information such as blood pressure, weight, height, BMI, etc. Risk factors can include smoking history, family cardiovascular disease (CVD), family cancer instance, diabetes, chronic renal disease, atrial fibrillation, etc. The risk breakdown by changeable factors graphic can be displayed as a ring or "doughnut", and can include changeable contributions and unchangeable contributions. Changeable contributions can include lowering cholesterol, lowering blood pressure, smoking cessation, lowering BMI, etc. Unchangeable factors can include smoking history, ethnicity, family history, and so on.

In a usage scenario, a content production pipeline can perform tasks for a medical content factory. The tasks can include high-level techniques for content production. The techniques can include definitions of medical content that can be covered, where the medical content can include medical guidelines, diseases, sources, and so on. Various techniques can be used for extracting the medical content from a range of sources such as medical databases, peer reviewed research, digests of papers, etc. The techniques can also include evaluation of the medical content for accuracy, efficacy, and the like, while other techniques can include implementation of the medical content factory. In the scenario described, there are four main characters presented. These characters can include a medical board that may include medical and technological personnel, a content manager, a content specialist, and a content producer. The roles of these characters can include the medical board defining and prioritizing the medical content to be covered; the content manager gathering guideline content, such as documents and papers, assigning the guideline content to the content specialist, and reviewing and approving intermediate production steps; the content specialist scoping the general structure of a rule, extracting inputs, outputs, and excerpts from the document; and the content producer generating medical rules into a platform and submitting the rules for approval.

The usage scenario can include one or more steps for medical content production. The scenario can include the medical board analyzing and prioritizing guidelines, diseases, sources, and so on. The medical board can choose one or more diseases, conditions, etc., that can be addressed by the medical content. The content manager can select guideline documentation and recommend it for review by the medical board. The content manager can survey medical databases, research results, papers, etc., selecting ones she or he thinks are relevant, and referring the selected guideline documentation to the medical board. The medical board can review the selected guideline documentation and either approve or disapprove the guideline documentation. If approved, the content manager can upload the documents into a database, and assign a content specialist to each uploaded document.

The documents assigned to the content specialists are processed. A content specialist is notified that documents are available and begins processing the documents. The content specialist highlights relevant parts of the assigned documents, and for each highlighted part, scopes the main disease or medical problem, any inputs, any outputs, and any related diseases or medical problems. The content specialist submits the scoped documents to the content manager, and if approved by the content manager, the document is sent to the content producer. The content producer is notified that the document is available. The content producer can parse the scoped content into a rule. The rule can be a logic rule, a Boolean equation, etc. The content manager receives the parsed rule and reviews the rule. When approved by the content manager, the parsed rule goes to testing and a quality assurance (QA) environment. The content specialist and the content manager test the rule with patient data. When both the content specialist and the content manager approve the rule, the rule is sent to the medical board for review. The medical board approves the rule. The rule is deployed to the production environment and made available for use. The rule becomes available for general use.

Figure 12:
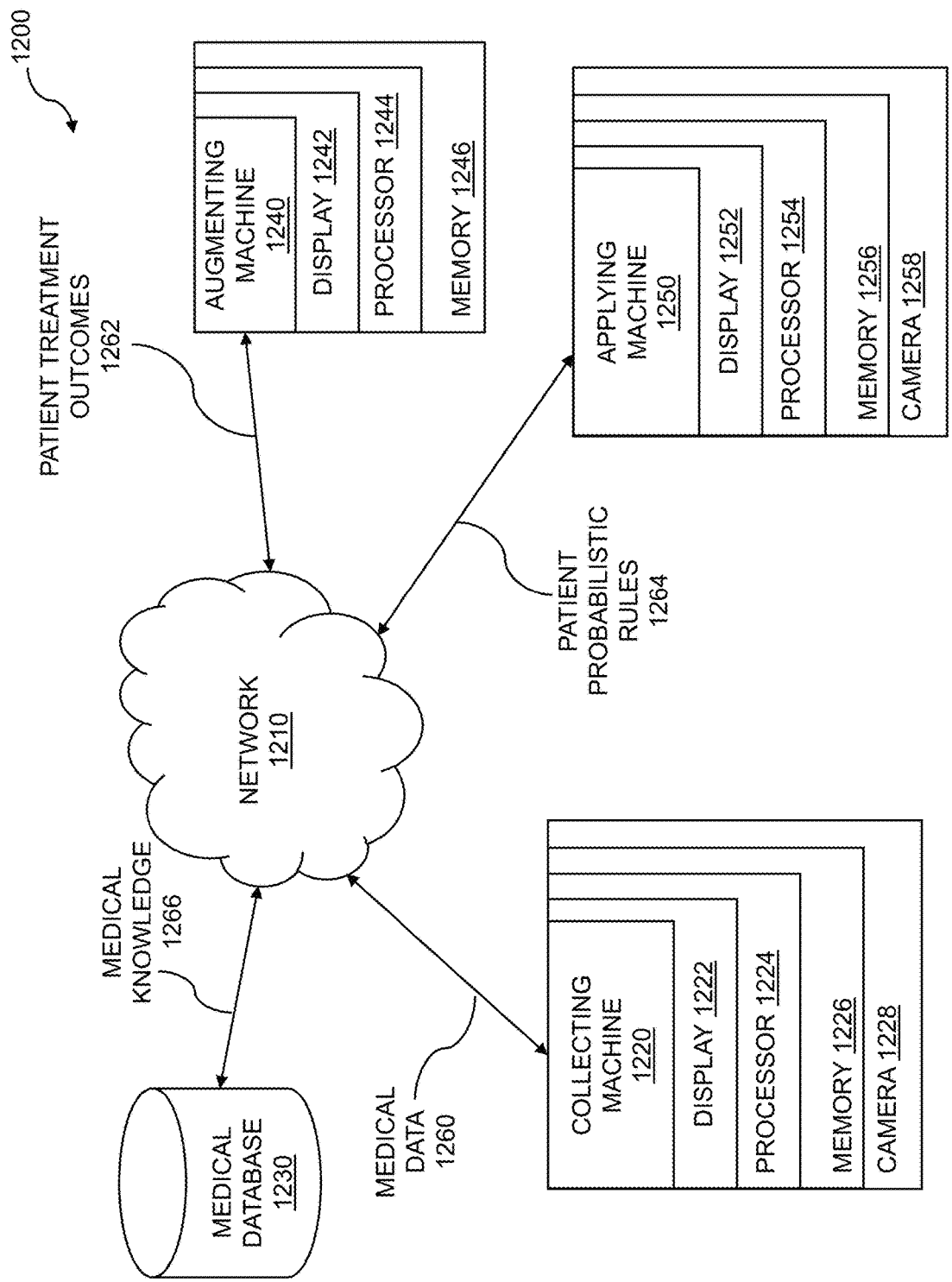
FIG. 12 is a system for machine learning for collaborative medical data metrics.

FIG. 12 is a system for machine-learning for collaborative medical data metrics. The system for machine-learning for collaborative medical data metrics can include collecting medical data from a plurality of clinicians serving a first plurality of patients and assembling a medical knowledge database that includes medical knowledge information, medical diagnoses, and medical treatments. The medical knowledge database can be a function of demographics and can include a medical probabilistic rules graph. The system for machine-learning for collaborative medical data metrics can include augmenting the medical knowledge base. The augmenting can include augmenting the medical knowledge database based on further medical data collected from a second plurality of clinicians. The further medical data can be based on individual patient treatment outcomes collected by the second plurality of clinicians. The system for machine-learning for collaborative medical data metrics can include applying medical data from a further patient to the medical probabilistic rules graph that was augmented to produce a medical diagnosis. The system for machine-learning for collaborative medical data metrics can further include projecting an impact for the further patient due to a change in medical treatment.

The system 1200 for machine-learning for collaborative medical data metrics can be implemented using a variety of electronic hardware and software techniques. For example, the system 1200 can be implemented using one or more machines. The system 1200 can include a computer system for machine-learned collaborative medical diagnosis comprising: a memory which stores instructions; one or more processors attached to the memory wherein the one or more processors, when executing the instructions which are stored, are configured to: collect medical data from a plurality of clinicians serving a first plurality of patients and assemble a medical knowledge database that includes medical knowledge information, medical diagnoses, and medical treatments, wherein the medical knowledge database is a function of demographics and comprises a medical probabilistic rules graph; augment the medical knowledge database based on further medical data collected from a second plurality of clinicians, wherein the further medical data is based on individual patient treatment outcomes collected by the second plurality of clinicians; and apply medical data from a further patient to the medical probabilistic rules graph that was augmented to produce a medical diagnosis.

The system 1200 can include one or more collecting machines 1220 linked to a medical database 1230. The one or more collecting machines 1220 can be linked to a medical database 1230 via a network 1210 such as the Internet or another computer network. The medical database can include a medical knowledge database, where the medical knowledge database can include medical knowledge information, medical diagnoses, and medical treatments. The medical knowledge database can be a function of demographics and comprises a medical probabilistic rules graph. The network can be wired or wireless, a combination of wired and wireless networks, and so on. The one or more collecting machines 1220 can be linked to one or more augmenting machines 1240 via the network 1210 or another computer network. The augmenting machines can augment the medical knowledge database based on further medical data collected from a second plurality of clinicians. The further medical data can be based on individual patient treatment outcomes collected by the second plurality of clinicians. The augmenting machine 1240 can be linked to one or more applying machines 1250, also via the network 1210 or another computer network. The medical data 1260 from the collecting machine 1220, the patient treatment outcomes 1262 from the augmenting machine 1240, the patient probabilistic rules 1264 from the applying machine, and the medical knowledge 1266 from the medical database 1230 can each be transferred to and/or from the other machines via the network 1210 or another computer network. The other computer network can be public or private, wired or wireless, high-speed or low-speed, and so on.

The collecting machine 1220 can comprise a server computer, a smartphone, a tablet, a PDA, a laptop computer, a desktop computer, a data center, a cloud computing service, and so on. In embodiments, collecting machine 1220 comprises one or more processors 1224 coupled to a memory 1226 which can store and retrieve instructions, a display 1222, and an optional camera 1228. The camera 1228 can include a webcam, a video camera, a still camera, a thermal imager, a CCD device, a phone camera, a threedimensional camera, a depth camera, a light field camera, a plenoptic camera, multiple webcams used to show different views of a person, or any other type of image capture technique that can allow captured data to be used in an electronic system, such as a scanner or bar code reader. The memory 1226 can be used for storing instructions, patient data, etc. The display 1222 can be any electronic display, including but not limited to, a computer display, a laptop screen, a net-book screen, a tablet computer screen, a smartphone display, a mobile device display, a remote with a display, a television, a projector, or the like. The medical data 1260 can be transferred via the network 1210, or other computer network, for a variety of purposes including analysis, augmenting, sharing, rendering, storage, cloud storage, and so on.

The augmenting machine 1240 can comprise a server computer, a smartphone, a tablet, a PDA, a laptop computer, a desktop computer, a data center, a cloud computing service, and so on. In embodiments, the augmenting machine 1240 comprises one or more processors 1244 coupled to a memory 1246 which can store and retrieve instructions, and a display 1242. The memory 1246 can be used for storing instructions, patient data, etc. The display 1242 can be any electronic display, including but not limited to, a computer display, a laptop screen, a net-book screen, a tablet computer screen, a smartphone display, a mobile device display, a remote with a display, a television, a projector, or the like. Patient treatment outcomes 1262 can be transferred via the network 1210, or other computer network, for a variety of purposes including analysis, sharing, rendering, storage, cloud storage, and so on.

The applying machine 1250 can comprise a server computer, a smartphone, a tablet, a PDA, a laptop computer, a desktop computer, a data center, a cloud computing service, and so on. In embodiments, applying machine 1250 comprises one or more processors 1254 coupled to a memory 1256 which can store and retrieve instructions, a display 1252, and an optional camera 1258. The memory 1256 can be used for storing instructions, patient data, etc. The display 1252 can be any electronic display, including but not limited to, a computer display, a laptop screen, a net-book screen, a tablet computer screen, a smartphone display, a mobile device display, a remote with a display, a television, a projector, or the like. Patient probabilistic rules 1264 can be transferred via the network 1210, or other computer network, for a variety of purposes including analysis, sharing, rendering, storage, cloud storage, and so on.

The system 1200 can include a computer program product embodied in a non-transitory computer readable medium for machine learned collaborative medical diagnosis, the computer program product comprising code which causes one or more processors to perform operations of: collecting medical data from a plurality of clinicians serving a first plurality of patients and assembling a medical knowledge database that includes medical knowledge information, medical diagnoses, and medical treatments, wherein the medical knowledge database is a function of demographics and comprises a medical probabilistic rules graph; augmenting the medical knowledge database based on further medical data collected from a second plurality of clinicians, wherein the further medical data is based on individual patient treatment outcomes collected by the second plurality of clinicians; applying medical data from a further patient to the medical probabilistic rules graph that was augmented; and providing a medical diagnosis, based on the medical data applied from a further patient to the medical probabilistic rules graph.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"— may be implemented by computer program instructions, by special-purpose hardware-based computer systems, by combinations of special purpose hardware and computer instructions, by combinations of general purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate, the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc;

an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. A computer-implemented method for machine-learned collaborative medical diagnosis comprising:
    collecting medical data from a plurality of clinicians serving a first plurality of patients and assembling a medical knowledge database using a neural network to perform machine learning, wherein the database includes medical knowledge information, medical diagnoses, and medical treatments, wherein the medical knowledge database contains data representing a plurality of edges and nodes that comprise a medical probabilistic directed acyclic rules graph generated by the neural network;
    pruning the medical probabilistic directed acyclic rules graph by removing paths having a probability below a predetermined threshold;
    augmenting the medical knowledge database and the medical probabilistic directed acyclic rules graph by training the neural network based on further medical data collected from a second plurality of clinicians, wherein the further medical data is based on individual patient treatment outcomes collected by the second plurality of clinicians;
    applying medical data from a further patient to the medical probabilistic directed acyclic rules graph that was augmented by training the neural network; and
    providing a medical diagnosis for the further patient, based on the medical data applied from the further patient to the medical probabilistic directed acyclic rules graph generated by the neural network.

2. The method of claim 1 wherein the medical diagnosis is used to institute a treatment plan.

3. The method of claim 2 wherein the treatment plan that was instituted comprises a change in treatment.

4. The method of claim 1 wherein the medical diagnosis comprises a list of evidence-based treatments, lab work recommendations, diagnostic recommendations, or lifestyle interventions.

5. The method of claim 1 wherein the medical diagnosis provides evidence-based gaps in care or errors in treatment plans.

6. The method of claim 1 wherein the collecting, the augmenting, the applying, and the providing comprise machine learning medical analysis.

7. The method of claim 1 further comprising further augmenting the medical knowledge database based on non-medical data.

8. The method of claim 7 further comprising applying further non-medical data from the further patient to the medical probabilistic rules graph, wherein the medical probabilistic rules graph has been updated based on the medical knowledge database that was further augmented.

9. The method of claim 1 further comprising projecting an impact for the further patient due to a change in medical treatment.

10. The method of claim 1 further comprising projecting an impact due to a change in behavior.

11. The method of claim 1 further comprising generating a treatment plan for the further patient based on the medical probabilistic rules graph that was augmented.

12. The method of claim 11 wherein the further patient is within the first plurality of patients or a second plurality of patients.

13. The method of claim 11 wherein the treatment plan for the further patient is further based on health background descriptors.

14. The method of claim 1 wherein there is overlap between the first plurality of patients and a second plurality of patients.

15. The method of claim 1 further comprising performing a query by a clinician of the medical knowledge database.

16. The method of claim 15 wherein the query is based on demographic data from an additional further patient.

17. The method of claim 16 wherein the query results in a diagnosis for the additional further patient.

18. The method of claim 1 wherein the plurality of clinicians and the second plurality of clinicians have one or more clinicians in common.

19. The method of claim 1 wherein the augmenting the medical knowledge database is accomplished with a deep learning system.

20. The method of claim 19 further comprising mapping a medical treatment to efficacy using the deep learning system.

21. The method of claim 19 further comprising determining an anticipated medical outcome based on a medical treatment and a clinical state for the further patient.

22. The method of claim 1 wherein the assembling the medical knowledge database includes generating medical rules based on the medical knowledge information.

23. The method of claim 22 wherein a subset of the medical rules is included in the medical probabilistic rules graph.

24. The method of claim 23 wherein the medical rules apply rules within the subset of the medical rules in a specific order based on an ordering.

25. The method of claim 1 further comprising providing feedback to improve the medical knowledge information based on evaluating treatment results.

26. A computer program product embodied in a non-transitory computer readable medium for machine learned collaborative medical diagnosis, the computer program product comprising code which causes one or more processors to perform operations of:
- collecting medical data from a plurality of clinicians serving a first plurality of patients and assembling a medical knowledge database using a neural network to perform machine learning, wherein the database includes medical knowledge information, medical diagnoses, and medical treatments, wherein the medical knowledge database contains data representing a plurality of edges and nodes that comprise a medical probabilistic directed acyclic rules graph generated by the neural network;
- pruning the medical probabilistic directed acyclic rules graph by removing paths having a probability below a predetermined threshold;
- augmenting the medical knowledge database and the medical probabilistic directed acyclic rules graph by training the neural network based on further medical data collected from a second plurality of clinicians, wherein the further medical data is based on individual patient treatment outcomes collected by the second plurality of clinicians;
- applying medical data from a further patient to the medical probabilistic directed acyclic rules graph that was augmented by training the neural network; and
- providing a medical diagnosis for the further patient, based on the medical data applied from the further patient to the medical probabilistic directed acyclic rules graph generated by the neural network.

27. A computer system for machine learned collaborative medical diagnosis comprising:
- a memory which stores instructions;
- one or more processors attached to the memory wherein the one or more processors, when executing the instructions which are stored, are configured to:
  - collect medical data from a plurality of clinicians serving a first plurality of patients and assembling a medical knowledge database using a neural network to perform machine learning, wherein the database includes medical knowledge information, medical diagnoses, and medical treatments, wherein the medical knowledge database contains data representing a plurality of edges and nodes that comprise a medical probabilistic directed acyclic rules graph generated by the neural network;
  - augment the medical knowledge database and the medical probabilistic directed acyclic rules graph by training the neural network based on further medical data collected from a second plurality of clinicians, wherein the further medical data is based on individual patient treatment outcomes collected by the second plurality of clinicians;
  - apply medical data from a further patient to the medical probabilistic directed acyclic rules graph that was augmented by training the neural network; and
  - provide a medical diagnosis for the further patient, based on the medical data applied from the further patient to the medical probabilistic directed acyclic rules graph generated by the neural network.

* * * * *